United States Patent
Fischer

(10) Patent No.: US 11,867,666 B2
(45) Date of Patent: Jan. 9, 2024

(54) MEASURING SYSTEM, MEASURING ARRANGEMENT AND METHOD FOR DETERMINING MEASURING SIGNALS DURING A PENETRATION MOVEMENT OF A PENETRATION BODY INTO A SURFACE OF A TEST BODY

(71) Applicant: HELMUT FISCHER GMBH INSTITUT FÜR ELEKTRONIK UND MESSTECHNIK, Sindelfingen (DE)

(72) Inventor: Helmut Fischer, Oberägeri (CH)

( * ) Notice: Subject to any disclaimer, the term of this patent is extended or adjusted under 35 U.S.C. 154(b) by 0 days.

(21) Appl. No.: 17/455,984

(22) Filed: Nov. 22, 2021

(65) Prior Publication Data

US 2022/0074838 A1     Mar. 10, 2022

(51) Int. Cl.
*G01N 3/46* (2006.01)
*G01N 33/00* (2006.01)

(52) U.S. Cl.
CPC ....... *G01N 3/46* (2013.01); *G01N 2033/0096* (2013.01); *G01N 2203/005* (2013.01); *G01N 2203/0282* (2013.01); *G01N 2203/0286* (2013.01); *G01N 2203/0635* (2013.01)

(58) Field of Classification Search
CPC ............ G01N 3/46; G01N 2203/0286; G01N 2203/0282; G01N 2033/0096; G01N 3/40; G01N 3/42; G01N 3/44; G01N 3/48; G01B 7/34
USPC ............................ 73/7, 78, 81–84, 104, 105
See application file for complete search history.

(56) References Cited

U.S. PATENT DOCUMENTS

2001/0031077 A1    10/2001    Souluer

FOREIGN PATENT DOCUMENTS

DE      3738106      5/1989
DE      69917780      6/2005

*Primary Examiner* — Robert R Raevis
(74) *Attorney, Agent, or Firm* — Mark Wisnosky

(57) ABSTRACT

A measuring device for detecting measuring signals during either a scanning across a surface to determine a surface profile or a penetration movement of an indenter into a surface of the specimen to determine hardness, and, scanning with sufficient force to determine the scratch resistance of the specimen is described. All of the measurements can be done on the same specimen without unmounting the specimen from a holder. A camera mounted to the same framework as the measuring device enables further documentation of the specimen being tested.

20 Claims, 15 Drawing Sheets

MEASURING SYSTEM, MEASURING ARRANGEMENT AND METHOD FOR DETERMINING MEASURING SIGNALS DURING A PENETRATION MOVEMENT OF A PENETRATION BODY INTO A SURFACE OF A TEST BODY

CROSS-REFERENCE TO RELATED APPLICATIONS

This application is a continuation in part of U.S. application Ser. No. 16/464,395 with the same title and same inventor, filed 28 May 2019 and currently pending.

STATEMENT REGARDING FEDERALLY SPONSORED RESEARCH OR DEVELOPMENT

Not Applicable.

BACKGROUND OF THE INVENTION

Field of the Invention

The invention relates to a measuring device, as well as a measuring arrangement and a method for detecting measuring signals during a penetrating movement of an indenter into a surface of a specimen, as well as for determining the scratch resistance of the surface of the specimen, as well as for determining the surface roughness of the specimen.

Description of Related Art

From DE 699 17 780 T2, a measuring means as well as a method for measuring the scratch resistance of a surface of a specimen are known, which comprise a measuring table for receiving a specimen as well as a handling means for transferring the measuring device from an initial position into a measuring position. In addition, a control is provided, through which the measuring device, after having placed a specimen on the surface to be tested, actuates both a displacement movement of the measuring table along an axis as well as a penetrating movement of the indenter is actuated, such that, during the displacement movement of the measuring table, the indenter penetrates the surface of the specimen.

For the actuation of the penetrating movement of the indenter after being placed on to the surface of the specimen, the measuring device comprises a piezoelectric actuator which acts on a first retaining plate, which plate is movable upwards and downwards by means of two leaf spring pairs. Said holding plate receives another plate, which, in turn, is movably-mounted, upwards and downwards, by means of two leaf spring pairs, with said plate having the indenter arranged therein. A measuring device is provided between the holding plate and the plate that receives the indenter, said measuring device measuring the penetration path. In addition, a measuring device is arranged next to it, for determining the normal force.

This measuring device comes with the disadvantage that, between the piezoelectric actuator and the penetrating tip, a structure that is of heavy and elaborate construction is provided by the holding plate as well as by the plate receiving the indenter, by the leaf spring pairs in each case selected for the mounting. Not only a large construction space is thereby required, but the piezoelectric drive is to be designed correspondingly large, in order to provide the force for actuating the penetrating movement. Furthermore, this measuring device is sluggish, owing to the elaborate constructive structure. Furthermore, the measuring device, due to the actuation of the indenter by means of a high-precision actuator, is expensive.

BRIEF SUMMARY OF THE INVENTION

The object underlying the invention is to create a measuring device for detecting measuring signals during a penetration movement of an indenter into a surface of the specimen, in particular for determining the scratch resistance of the surface or for detecting measuring signals during a scanning movement of an indenter on the surface of a specimen, in particular for determining the surface roughness of the specimen, as well as providing a measurement device and a method for determining measuring signals during a penetrating movement of the indenter, in particular for determining the scratch resistance of the surface of the specimen, or during a scanning movement of the indenter, whereby an increased measurement precision and reduced costs are enabled.

The object underlying the invention is achieved by a measuring device with an indenter and a force generation means, with which the indenter is operatively coupled, in which the indenter penetrates into a surface to be measured of the specimen or scans a surface to be measured of the specimen. At least one measuring means is provided for measuring the penetration depth and the surface roughness. The penetration movement of the indenter or the scanning movement of the indenter can be driven by means of the force generation means using magnetic force. The use of a such force generation means, which includes a drive means and a magnetic transmission means, in which the penetration movement or scanning movement of the indenter is driven by means of a magnetic force, has the advantage, that a physical decoupling of drive means and indenter is given. This allows for a frictionless transmission of force from the drive onto the indenter. In addition, a change in magnetic force is directly translated into a penetration movement of the indenter into the surface of the specimen or into a contact force for a scanning movement of the indenter. The increase of magnetic forces thus means a direct increase of the force for the indenter and vice versa. Through the configuration of the force generation means with a magnetic force, a hysteresis-free driving of the penetration movement of the indenter is thus allowed for. In addition, temperature impacts can be excluded by means of the force generation means. Moreover, further disadvantageous impacts are also excluded, as the magnetic force cannot be compressed. Through the force transmission activatable without hysteresis, an exact setting and/or high repeatability of a penetration force or contact force for a scanning movement of the indenter can be settable. In addition, an arrangement of a force generation means, reduced in terms of mass, can be achieved. Also, such a force generation means comes with the advantage that a once-set magnetic force can be kept constant.

The magnetic transmission means of the measuring device preferably comprises a first and a second magnetic pole, which are arranged spaced to and opposite one another, wherein the magnetic poles are oriented one with respect to the other with the same poles. Preferably, permanent magnets are provided. The first and second magnetic poles can be configured by one or multiple permanent magnets, which can be oriented together or spaced from one another. E.g. two magnets spaced from one another or e.g. three permanent magnets arranged on a circle can form a first and/or second magnetic pole. This way, a repulsive force can be generated between the first and second magnetic poles. As the respective magnetic fields of the magnetic poles can not be compressed, a defined increase of force can be produced and achieved with increasing decrease of the distance, which increase is provided for a displacement movement of the indenter.

It is preferably provided for the second magnetic pole to be provided on the transmission element receiving the indenter on the opposite end thereof, wherein the transmission element is guided, inside the housing, displaceably along a travel axis. The travel axis is preferably oriented perpendicular to a base plate of the housing, or the travel axis is preferably located in the axis of the indenting movement of the indenter. Here, a magnetic force acting lengthwise to the drive element can be translated into a displacement movement along the longitudinal axis of the transmission element. This allows for an arrangement and a force transmission free from any losses.

The first magnetic pole of the magnetic force transmission means is preferably connected with the drive means, through which a displacement movement of the first magnetic pole along a travel axis is driven. This travel axis may be located in the axis of the indenting movement of the indenter or parallel thereto. A displacing movement of the first magnetic pole directly towards the second magnetic pole is thereby driven, wherein, in particular with a congruence of the travel axes, a particularly suitable, in particular non-tilt transmission of force of the magnetic force from the first magnetic pole onto the second magnetic pole is given. Alternatively, the travel axis of the first magnetic pole can be oriented perpendicular to the axis of the indenting movement of the indenter. The travel axis of the indenter is usually oriented perpendicular to the surface of the object to be measured and is thusly preferably located in the vertical. In the alternative embodiment, the travel axis of the first magnetic pole thusly lies in the horizontal. Such an arrangement has the advantage that a low-profile measuring device can be created.

It is preferably provided that, by a displacing movement of the first magnetic pole in the direction towards the second magnetic pole, the displacing movement of the indenter in the direction towards the specimen and a penetration force into the specimen or a contact force for scanning the surface of the specimen can be adjusted. Simple relationships are given thereby, wherein merely by a feed motion of the first magnetic pole, the driving of the indenter via the second magnetic pole is enabled.

It is preferably provided, that the transmission element is of pin-type or tubular design. A rigid configuration of the transmission element as well as a lightweight embodiment can thereby be achieved.

Preferably, the transmission element is displaceably received by means of a guide, said guide being fixed to a holding device in the housing. This guide preferably comprises at least two resilient elements that are spaced apart from one another, in particular two leaf spring elements spaced in parallel to one another, or two pressure diaphragm elements spaced in parallel to one another, which are guided in a manner to be displaceable in the travel axis of the drive device or are deflectable along the travel axis. The leaf-spring elements or pressure diaphragm elements engage, on the one hand, on the transmission element and are, with the opposite end thereof, held on a holding device of the housing. The guide is preferably made from non-magnetizable materials.

According to a first embodiment, it can be provided that the leaf spring elements or pressure diaphragm elements of the holding device are held in a tightly-clamped manner. This allows for the leaf spring elements or the pressure diaphragm elements to be adaptable to the respective task and/or size of the measuring device, in a simple manner, by exchanging them. In addition, a modular construction can be brought about.

Alternatively, it can be provided that the holding device and the leaf spring device are formed as one piece and preferably, the leaf spring elements are produced by erosion or ultrafine processing. Such an arrangement allows for a compact design, in which simultaneously a displacement movement of the leaf spring elements is limited by an intermediate body of the holding device extending between the leaf spring element.

The spring leaf elements preferably comprise a clamping region assigned to the holding device and, opposite thereto, a receiving region acting on the transmission pin as well as a spacer portion located therein between, wherein the clamping region and the spacer portion, as well as the receiving region and the spacer portion are respectively connected to one another by means of a flexure bearing. This arrangement comes with the advantage, that the clamping region and the receiving region can substantially remain in parallel orientation upon a deflection of the leaf spring element. Advantageously, it is provided that the flexure bearings are configured as hinges, being resilient in one spatial direction and being rigid in the other two spatial directions. The latter can be reduced in thickness with respect to the clamping region, the receiving region and the spacer portion. Owing to the thickness of the flexure bearings, the force to be applied can be destined for deflecting the leaf spring elements.

One advantageous configuration of the flexure bearings in the leaf spring elements provides that the latter extend over the entire width of the leaf spring element and preferably comprise at least one slot recess. By such a slot recess, in turn, the force for a deflecting movement can be adaptable in a simple manner and can be reduced.

The housing of the measuring device preferably comprises a baseplate with a recess, along the longitudinal axis of which the displacement movement of the indenter is directed, wherein the indenter can be guided through the opening and can be positioned in a position protruding to the outside with respect to the base plate. This way, a drive shaft of the drive device for driving the displacing movement of the indenter as well as a longitudinal axis of the transmission element receiving the indenter, can be located on a common axis. This allows for an immediate and direct driving of the displacing movement of the indenter.

Preferably, it is provided that the guide holds the transmission element and the indenter arranged thereon in an initial position, in which the indenter is arranged set back towards the inside with respect to a lower side of the housing, which is oriented towards the specimen. This comes with the advantage of providing protection against damage of the indenter. Preferably, in this initial position, the transmission element is kept in balance with the magnetic pole provided thereon in the receiving element and the opposite indenter. The indenter is preferably positioned inside an opening in the base plate of the housing. Furthermore, an attachment ring can also be positioned within said opening, which ring comprises a through hole. The attachment ring can protrude with respect to the lower side of the housing, however, the indenter is preferably set back towards the inside also with respect to an attachment surface of the attachment ring, in the initial position.

Preferably a first measuring means, in particular a distance sensor, is provided adjacent to the recess in the base plate of the housing, which device comprises a measuring probe or first sensor element attached to an internal end of the indenter and a second sensor element fixed to the housing. During a displacing movement or a penetrating movement of the indenter into the specimen, the actual displacing movement can thereby be detected by the distance between the first and second sensor elements, and, via the evaluation of the hardness of the specimen or of a scratch or also for determining the surface roughness, are detected and are forwarded to a control device. In one embodiment the first sensor element is a ferrite ring and the second sensor element comprises a coil and an eddy current is generated when the first sensor moves relative to the second sensor element. In another embodiment the first sensor element includes an optical encoded strip such as a grating or reticle and the second sensor element includes an optical sensor. The first measuring means includes a first sensor that moves with the indenter and a second sensor fixed to the housing and the distance between the two sensor elements is determined either electronically or optically. The distance measurement data is sent to the control device.

The drive means of the force generation means is advantageously provided on a cover element of the housing provided opposite the base plate, which element comprises at least one length-adjustable drive element, preferably located in a travel axis of the displacing movement of the indenter. This comes with the advantage, that the induction a force for generating a displacing movement finds itself in the travel axis of the indenter, so that losses can be minimized.

The drive element receives the first magnetic pole at an end directed towards the transmission pin. This comes with the advantage that, by a defined displacing movement of the drive element, which is assigned to the cover element, a targeted change in distance to the opposite, respectively second magnetic pole can be set, that is, the increasing decrease of the distance goes along with an increase of the magnetic force.

The drive element is, for example, configured as a drive spindle and preferably guided, in a twist-proof manner, by means of a guide, wherein said guide in particular is provided on the cover element. The drive element can alternatively be configured as a telescopic spindle. The displacing movement of the drive element is driven by means of a rotary drive and a drive motor. Preferably, an electric drive motor is provided, which motor drives a rotary drive, in order to achieve a defined feed motion of the drive element and preferably to decode the feed motion in order to be able to exactly establish the travel path. in a preferred embodiment the electric drive motor is controlled by the control device. Alternatively to the electric drive, a pneumatic, hydraulic or electromagnetic drive can also be provided.

Advantageously, the rotary drive is configured as a toothed belt drive and drives the drive element that is twist-proof due to the guide. A configuration of simple construction is thereby provided. Due to the pitch of a thread on the drive spindle or of the threads from the telescopic spindle, a defined increase of a displacing movement can be set depending on the rotation.

A further alternative configuration of the measuring device provides that the travel axis of the drive element is oriented perpendicular to the travel axis of the indenter, and the drive element drives a displacing movement of the at least one first magnetic pole along the travel axis perpendicular to the travel axis of the indenter, until said first magnetic pole is transferred into a position with a partial overlap or a congruent position tow the second magnetic pole. Alternatively, it can be provided that the first magnetic pole is formed by two or more permanent magnets, which simultaneously is transferrable into a position with a partial overlap, or into a congruent position with respect to a corresponding number of permanent magnets forming the second magnetic pole. Insofar as, for example, two permanent magnets form a first magnetic pole, the second magnetic pole is likewise formed by two permanent magnets. By a simultaneous displacing movement of the permanent magnets forming the first magnetic pole, from a region outside of the magnetic field of the permanent magnets forming the second magnetic pole. into a position with a partial overlap or in a congruent arrangement, a uniform impact of the force field onto the two permanent magnets of the second magnetic pole is achieved. A non-tilt driving of a displacing movement of the transmission element can thereby be achieved along the travel axis of the indenter.

The drive element for the above-described alternative configuration of the measuring device preferably includes a pair of drive elements assigned to one another, in particular toothed racks, which are actuatable with a rotary drive perpendicular to the travel axis of the indenter and preferably are displaceable alongside guide rails. Said guide rails are oriented perpendicular to the displacing movement of the indenter, in particular perpendicular to the travel axis of the transmission element. On each drive element, in particular on each toothed rack a permanent magnet is provided, which together form a first magnetic pole. By such an arrangement, both drive elements, in particular toothed racks, can be driven with a drive wheel, whereby a synchronous displacing movement of the permanent magnets of the first magnetic pole, for the partial overlap or for congruent arrangement of the permanent magnets of the second magnetic pole, is driven. Advantageously, a drive shaft of the drive wheel of the two drive elements can be oriented slightly outside an angle of 90° to the travel direction of the drive elements. A play-free adjustment can thereby be achieved.

Furthermore, it is preferably provided in the alternative embodiment, that a receiving device is provided on the transmission element, which device receives at least one permanent magnet arranged in the travel axis or which receives two or more permanent magnets at the same distance to the travel axis of the transmission element for forming the second magnetic pole. Sufficient space is thereby provided, for example in order to move two permanent magnets of the second magnetic pole, e displaceable in the opposite of each other, towards the permanent magnets of the second magnetic pole and to position them in a congruent arrangement for maximum transmission of force.

Advantageously, the drive movement of the drive element is monitored with a third measuring means, in particular a rotary encoder. By knowledge of the magnetic flux of the magnetic poles, the increasing force can be determined with increasing and decreasing of the distance between the magnetic poles. Through this rotary encoder, it can be exactly detected, to change the distance of the magnetic poles, and thus, the force exerted onto the indenter, so that, by the control means, due to the travel path of the drive element, the force acting on the surface of the specimen is used as an evaluation parameter.

Another preferred configuration of the measuring device provides that a fourth measuring device, in particular a force sensor, is provided between the drive element and the magnetic pole arranged thereon. An additional monitoring of the force acting on the opposite magnetic pole on the transmission pin can be detected and/or monitored by the magnetic pole of the drive element.

Another preferred configuration provides that a vibration damping device is assigned to the magnetic pole arranged on the transmission element. Thereby, undesired lifting movements of the indenter, during a measuring with this measuring device can be reduced or prevented. This is in particular advantageous when determining the scratch resistance of a surface of the indenter.

According to a first embodiment, the vibration damping device is preferably configured by an enclosure, in particular a tube, made of a ferromagnetic material, which enclosure surrounds the second magnetic pole arranged on the transmission element, wherein the magnetic pole, in an initial position of the indenter, is least partially plunged into the vibration damping device. With increasing displacing movement of the indenter towards the specimen, the second magnetic pole is slightly moved out with respect to the vibration damping device, that is, that in a possible lift-off movement of the indenter from the specimen, a plunging of the magnetic pole into the vibration damping device results, which movement causes, an increase of the magnetic force and thus a counteracting of the plunging movement.

According to a further preferred embodiment of the measuring device, it is provided that a compensating element is provided between the two leaf spring elements spaced apart parallel to one another, which element is mounted on the holding device and protrudes, with one end thereof, into the transmission element, on which another leaf spring element is provided extending in the direction towards an end of the transmission pin receiving the magnetic pole and which is fastened thereto. Through this leaf spring element, a deflection movement of the transmission element can be counteracted in a displacing movement of the specimen relative to the indenter upon the determining of the scratch resistance. In addition, through this arrangement, an orientation of the transmission element in a basic position or initial position, within the housing of the measuring device, can also be achieved.

One preferred embodiment of the compensating element provides, that the latter is mounted on the holding device by means of a clamping strap mount. The levelling of the transmission pin can thereby be achieved in a basic or initial position.

Another preferred configuration of the measuring device provides, that the leaf spring element or pressure diaphragm element, arranged at a distance to the base plate, is tightly clamped in the holding device and that the leaf spring element or pressure diaphragm element arranged near the base plate is displaceably mounted with respect to a portion formed by longitudinal slots in a direction perpendicular to the travel axis of the transmission element. Preferably, a second measuring means is provided for detecting a displacing movement of the lower leaf spring element or portion of the pressure diaphragm element. Said second measuring means includes a sensor element, which detects a displacing movement of the lower leaf spring element or portion of the pressure diaphragm element during a displacing movement of the transmission element along the longitudinal axis thereof or the travel axis of the drive element. Likewise, a deflection of the transmission element can be established upon penetration of the indenter into the surface of the specimen during the performance of a scratch resistance test.

The object underlying the invention is further achieved by a measuring arrangement for detecting measuring signals during a displacing movement, in particular a penetration depth or a scanning movement, of an indenter in a surface or onto a surface of a specimen, in which a measuring table is provided on a base body or a base plate for receiving a specimen, as well as a handling means, in particular a stand receiving a measuring device that is transferred, via the handling means, into a position for the placement of an indenter onto the specimen, wherein the displacing movement, for penetration of the indenter into the surface of the specimen, or the displacing movement, for scanning the surface of the indenter, is driven and performed by a measuring device according to one or more of the above-desired features of the embodiments.

Furthermore, the measuring arrangement preferably receives an optical detection means adjacent to the measuring device, which optically captures and evaluates the point of penetration, the surface roughness or, when performing the scratch resistance test, the introduced scratch. Here, the measuring table is preferably displaceable between the measuring device and the optical detection means. Alternatively, the measuring device and the optical detection means can be displaceable towards the measuring table. In one embodiment, the optical detection means is a camera.

In addition, a displacing movement of the measuring table, in particular along a travel direction in the plane of the surface of the specimen, is driven by the control device while the control device simultaneously aquires data from the distance measuring devices and the encoder on the drive. Due to this control, a surface contour or roughness of the surface can thusly be detected upon placing the indenter onto the surface of the specimen, with said placement constituting a starting position, and in a subsequent, controlled displacing movement. This can also be performed for a pre-scan for establishing a scratch resistance. Likewise, a penetrating movement of the indenter can be driven during the displacing movement of the measuring table towards the indenter, starting from the starting position, in order to form a scratch. A post can for a scratch resistance test can also be driven starting from the starting position.

The object underlying the invention is furthermore achieved by a method for detecting measuring signals during a penetrating movement of an indenter into a surface of a specimen with a measuring device or during a scanning movement of an indenter on a surface of a specimen, in which the specimen is positioned on a measuring table, and the measuring device is placed onto the specimen, in that a penetrating movement of the indenter is driven with a force-generation means, in which, with a magnetic force, the penetrating movement of the indenter is driven into the specimen or, for a scanning movement, is driven on the specimen. This allows for a cost-effective configuration of the force generation means. In addition, an exact driving of the indenter can be achieved, as the force generation means is independent of fluctuations in temperature and has a small mass.

The restoring force of the leaf spring elements can be neglected in this case, or can be determined and considered depending on the travel path of the indenter along the travel axis thereof. The initial force, with which the force generating means acts upon the indenter, during the feed motion, up until placement upon the specimen, can, for example, be formed, on the one hand, by a force equilibrium between the restoring forces of the spring elements, and, on the other hand, by the displacing movement produced by the magnetic force in direction towards the indenter.

Preferably, a first method step is provided for a hardness measuring on a surface of the specimen, in which the measuring device is moved towards the specimen and, upon the placement of the measuring device, the feed motion is immobilized, wherein, subsequently, a displacing movement of the indenter is driven, which indenter, in an initial position, is set backwards inwardly with respect to an outer side of the measuring device, until this indenter is resting on the specimen, wherein this position is forwarded, to the control device, as the zero position for the subsequent hardness measuring. A defined initial situation for a measurement can thereby be achieved. In addition, the indenter is transferred out of a protected initial position into a measuring position. The detection of the zero position of the indenter, in which said indenter rests on the surface of the specimen, is advantageously detected by a first measuring means, which identifies that no change in path is specified, so that a signal is thereby forwarded to the control device, in order to immobilize the feed motion of the measuring device on to the specimen.

In addition, preferably a first method step is provided for a scratch resistance measurement, in which, prior to the indenter being placed on to the surface of the specimen, said indenter is applied with a feed force, so that the indenter, with respect to a lower side of the housing, freely protrudes to the outside. The measuring device is subsequently moved towards the specimen, and, upon placing of the indenter onto the specimen, the displacing movement of the measuring device is immobilized. Preferably, this position is, in turn, forwarded to the control device as a zero position, for the subsequent measuring of the scratch resistance.

Another preferred embodiment provides that, starting from the zero position of the indenter, the force generation means is acted upon with a testing force, and a penetrating movement of the indenter into the surface of the specimen is detected with a first measuring means. Through the change in path during the penetrating movement, as well as also by knowing the applied testing force, the hardness of the specimen is determined by the control device. At the same time, these measurement results can also be taken into account when measuring the scratch resistance.

Furthermore, it is preferably provided that a penetrating movement of the indenter is driven by a feed motion of the drive element of the drive means, and that a transmission of force occurs, from the drive element, onto the magnetic transmission element, or the indenter, respectively, by a magnetic transmission means.

In addition, it is preferably provided that the force, acting upon the indenter, is calculated or is detected by a fourth measuring means from the feed movement of the drive element, which is detected by the third measuring means, and that, by the first measuring means, the penetration depth of the indenter into the specimen is detected, and that, from the penetration force calculated or detected by the third or the fourth measuring means, and the penetration depth detected by the first measuring means, depending on the geometry of the indenter, at least the hardness of the surface of the specimen is identified. The fourth measuring means is preferably provided between the drive element of the drive device and the magnetic pole provided by the drive element.

In order to determine a scratch resistance of the surface of the specimen, the measuring table, with the specimen applied thereon, is preferably displaced, during the penetrating movement of the indenter, in a direction perpendicular to the penetrating movement of the indenter, and a scratch is introduced into the surface of the specimen. Measuring signals regarding the penetration depth are, through a first measuring means, detected depending on the time and the travel path. Furthermore, by means of a second measuring means of the measuring device, a deflection of the indenter, opposite the travel direction of the measuring table, is detected. In addition, a measuring force, acting upon the indenter, is forwarded, as a measuring signal, to the control device. Said measuring force can be determined from the feed motion of the drive element and the feed force of the indenter resulting from the magnetic transmission means into the surface. As an alternative, it can be provided for this determination of the measuring force, that measuring signals are detected by means of a fourth measuring means, wherein said fourth measuring means is positioned between a magnetic pole of the magnetic transmission device and the drive element, which accommodates said magnetic pole. From these detected signals can be identified the scratch resistance of a surface of the specimen.

Furthermore, additionally, a deflection of the indenter oriented at a right angle to the displacing movement of the measuring table is detected by another measuring device, preferably during the introduction of a scratch into the surface of the specimen. Thereby, an assessment regarding the surface of the specimen can additionally be made, and in particular, a statement about the homogeneity of the material can be achieved.

In addition, the measuring device is placed on to the surface, preferably prior to the introduction of a scratch into the specimen, is displaced in a direction perpendicular to the place-on movement of the specimen, and the surface is scanned. Signals are here detected by the first measuring device and are stored as a pre-scratch profile in the control device. Through a so-called pre-scan, the course of the surface of the specimen can be established, so that this further parameter can be taken into consideration in the subsequent determination of the scratch resistance.

In addition, performing a so-called post scan is provided for the determination of the scratch resistances. To that end, the measuring device is preferably placed on to the scratch after the scratch was introduced into the specimen, and the indenter is displaced with the measuring device in a direction perpendicular to the penetration movement of the specimen, that is, guided along in the scratch, and the detected measuring signals are stored in the memory of the control device.

Another preferred configuration of the invention provides that the test pressure in the force generation means is kept constant during the scanning movement of the indenter. Here, the indenter, under unchanged conditions, can be guided along the surface of the specimen, wherein the magnetic transmission device is then so to say formed as a rigid actuator, so that the displacing movement acting upon the indenter can be directly transmitted, due to the surface roughness, alongside the longitudinal axis of said indenter and can be detected by at least the first measuring means and the electrical signal from the first measuring means is transmitted to the control device.

The invention, as well as other advantageous embodiments and further developments thereof, are described in greater detail and explained in the following by means of the examples illustrated in the drawings. The features that can be taken from the description and the drawings can be used individually or in plural in any combination, according to the invention.

DETAILED DESCRIPTION OF THE INVENTION

Figure 1:
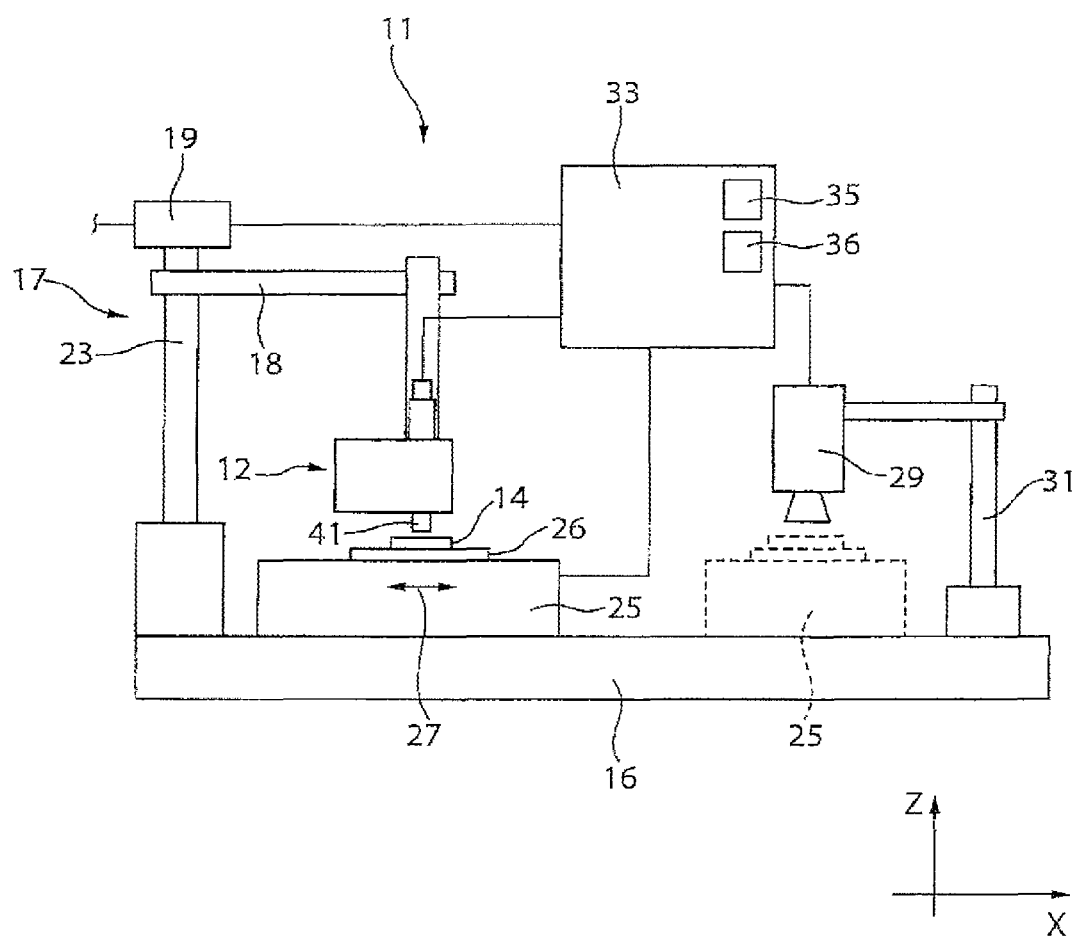
FIG. 1 a schematic view of a measuring arrangement according to the invention having a measuring device, FIG. 2 a first perspective view of the measuring device of FIG. 1, FIG. 3 a further perspective view of the measuring device according to FIG. 2, FIG. 4 a schematic side view of the measuring device according to FIG. 2, FIG. 5 a schematic, enlarged view of a lower part of the measuring device according to FIG. 2 with a first measuring means, FIG. 6 a schematic, enlarged view of an upper part of the measuring device according to FIG. 2 with a third measuring means, FIG. 7 a further schematic side view of the upper part of the measuring device according to FIG. 6, FIG. 8 a schematic, enlarged view of the measuring device with a second measuring means, FIG. 9 a schematic sectional view of an alternative embodiment of a lower part of the measuring device according to FIG. 5, FIG. 10 a perspective view onto a leaf spring element, FIG. 11 a perspective view onto an alternative embodiment of leaf spring element with a holding device for the measuring device according to FIG. 2, FIG. 12 a schematic side view of an alternative embodiment of the measuring device according to FIG. 2, FIG. 13 a schematic side view of a further alternative embodiment of the measuring device according to FIG. 2, FIG. 14: a schematic view from below onto a pressure diaphragm element of a holding device for the measuring device according to FIG. 13, FIG. 15 a perspective view of a further alternative embodiment of the measuring device according to FIG. 2, FIG. 16 a further schematic view onto the alternative measuring device according to FIG. 15, and FIG. 17 a schematic sectional view of the magnetic transmission device of the alternative measuring device according to FIG. 15.

FIG. 1 schematically illustrates a measuring arrangement 11. Such a measuring arrangement 11 can be provided for testing mechanical and/or physical properties of surfaces on specimens 14, such as for example films, layers and/or coatings on objects. The measuring arrangement 11 can, for example, be employed as a hardness measuring means, in which a hardness measurement is performed by penetration, by means of an indenter 41, of a measuring device 12. In addition, this measuring arrangement 11 with the measuring device 12 can be provided in order to determine a scratch resistance of a film, a layer or a coating on objects. CVD coatings or PVD coatings can be here tested with respect to their scratch resistance, for example. Likewise, further micro scratches can be detected or other deformation information from the surface can be detected and analyzed. Likewise, this measuring arrangement 11, in particular with the measuring device 12, also allows for a roughness measuring of a surface of the specimen 14, without being thusly accompanied by a damaging of the surface of the specimen 14. In this case, the indenter 41 is placed on to the surface of the specimen 14 and displaced along the surface in order to scan the roughness of the surface of the specimen 14.

The measuring arrangement 11 includes a common base body 16. Said body can preferably be formed of granite. A stand 17 is provided on the base body, which stand receives the measuring device 12 on a cantilever 18. Said stand 12 includes a drive motor 19, by means of which the measuring device 12 is displaceable from an initial position illustrated in FIG. 1 into a testing position 22, in which the indenter 41 rests on a specimen 14. The drive motor 19 can, for example, power the cantilever 18 for an up-and-down movement along a guide column 23 of the stand 12.

A measuring table 25 is additionally provided on the base body 16. Said measuring table 25 comprises a measuring table receptacle 26, which is driven at least in X direction according to arrow 27, in a displaceable manner. The specimen 14 is placed on to the measuring table receptacle 26 and fixed thereto.

The measuring arrangement 11 can furthermore include an optical detection means 29, which can likewise be arranged on the stand 17 or advantageously, separate therefrom, on another stand 31. This optical detection means 29 can be positioned adjacent to the measuring device 12. Here, the measuring table 25 or the measuring table receptacle 26 is configured to be displaceable in such a manner, that the specimen 14, after the introduction of a penetration location or a scratch into surface of the specimen 14, is displaceable towards the optical detection means 29, in order that the penetration location or the introduced scratch can be optically detected in the surface of the specimen 14. Alternatively, a displacing movement of the measuring device 12 and of the optical detection means 29 relative to the measuring table 25 can also be provided. In one embodiment, the optical detection means 29 is a camera. In a preferred embodiment the placement of the sample on to the measuring table receptacle fixes the sample location relative to the indenter and the various measuring means including the optical detection, such that the measurement locations are precisely known and sent to the control device. In one embodiment a surface profile is taken before and after a scratch test such that the location of the scratch is known and can be further characterized by the indenter to determine a profile of the scratch and by the optical detection device to further characterize the same location either photographically or otherwise optically.

The measuring device 11 further includes control device 33, which includes a data processing means (not shown in greater detail here), a display device 35 and an user input device 36. The control device 33 is, at least by signal lines, connected with the stand 17, the measuring device 12 and the measuring table 25. Preferably, the optical detection means 29, and, if necessary, the stand 31 receiving the optical detection device 29 is likewise connected thereto.

For driving the measuring device 12, the measuring arrangement 11 moreover comprises at least one control line, which is connected to the control device 33. The control device includes a computer processor, Input/output ports to accept data and send control signals from and to the measuring means, the drive motor for the indenter, the drive motor for the sample stage, the optical detection device, and, a user interface including display and input means. In one embodiment the control device further includes analog to digital (A/D) converters to accept analog, typically voltage, signals and convert to digital signals. The computer processor is programmed to accept the signals and calculate a surface profile, a hardness, and, a scratch resistance of the sample and to verify and further document the data with photographs of the sample using a camera as the optical detection device before and after measurements. Other optical measurements can also be made with other optical detection devices such as a spectrometer.

Figure 2:
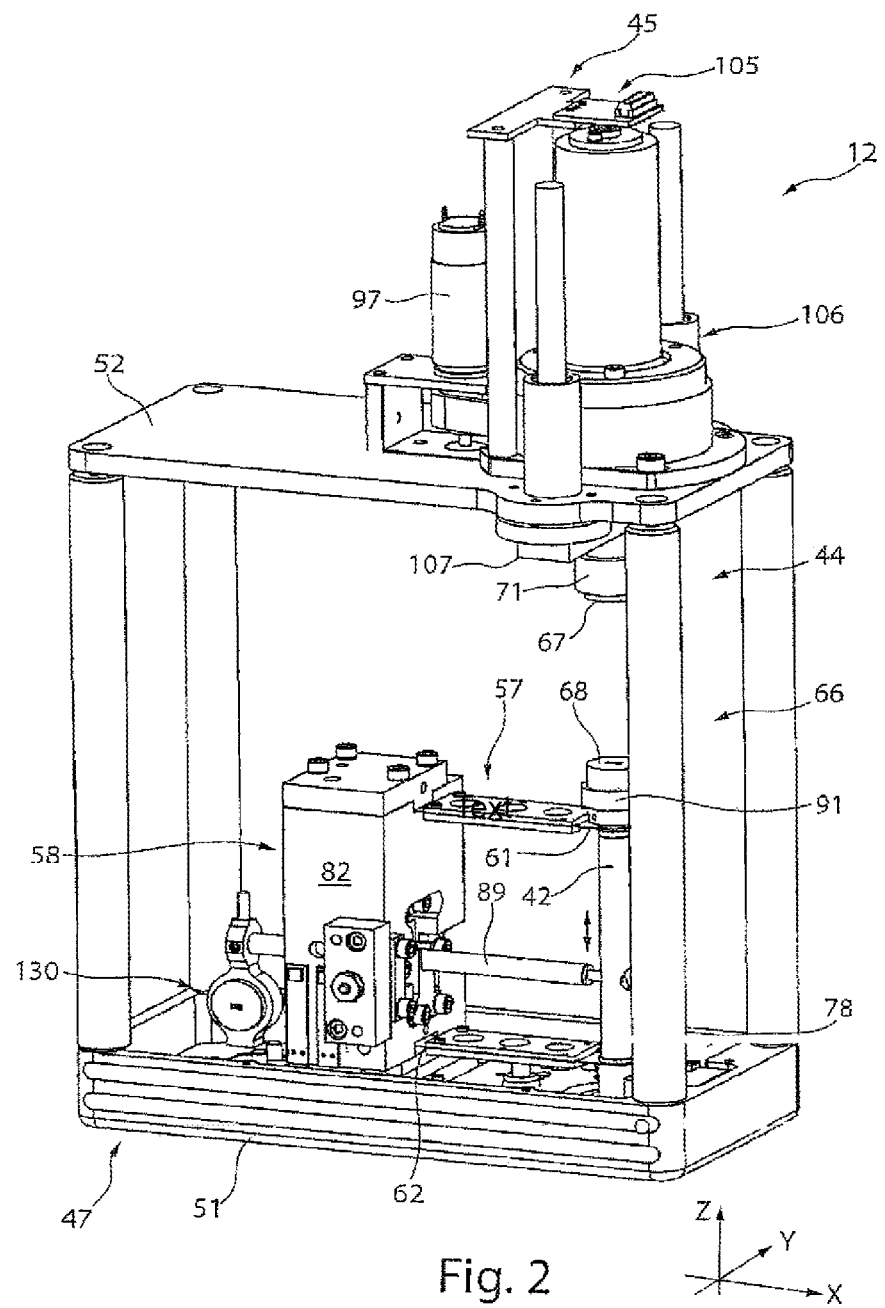
Figure 3:
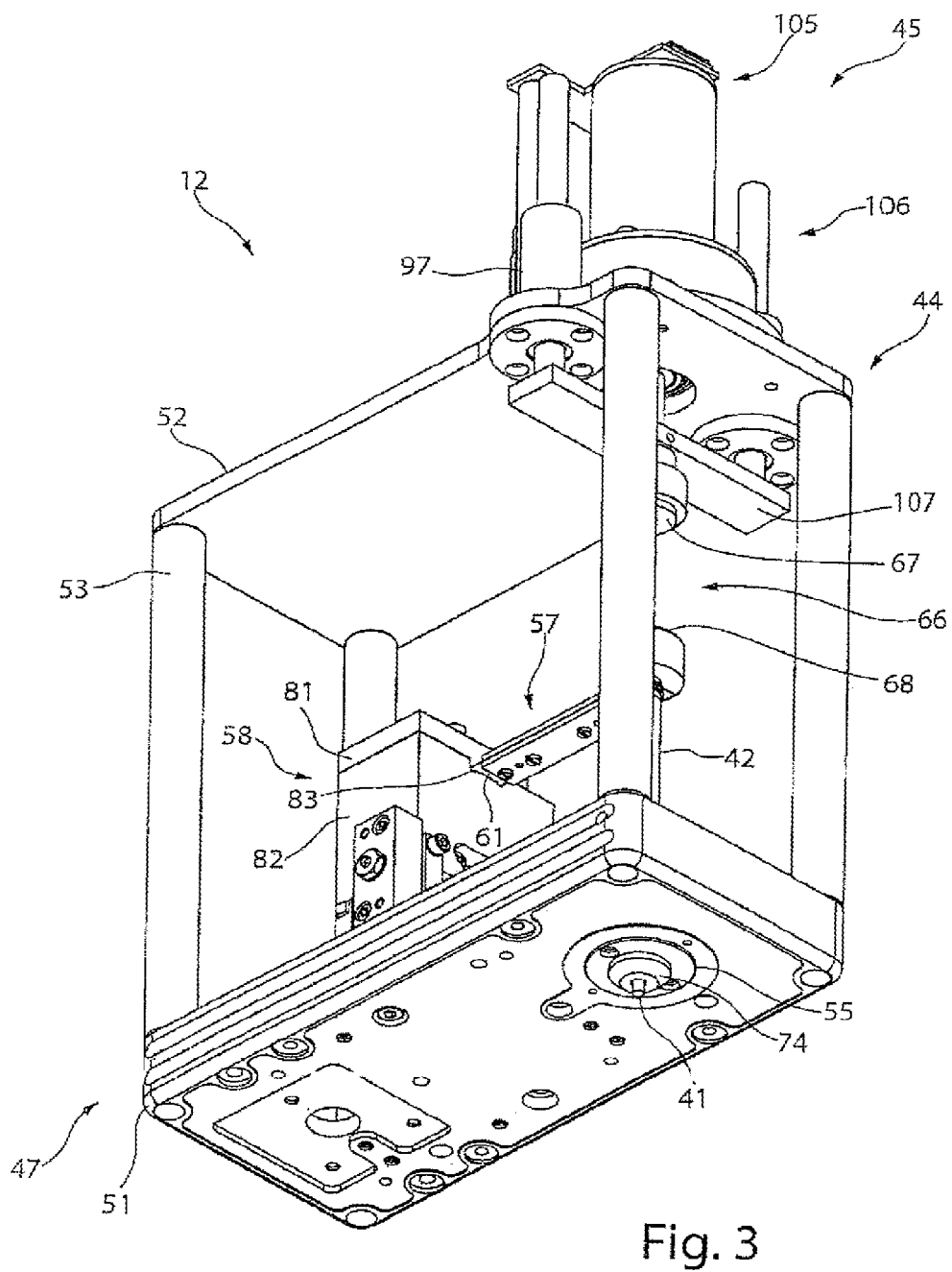
Figure 4:
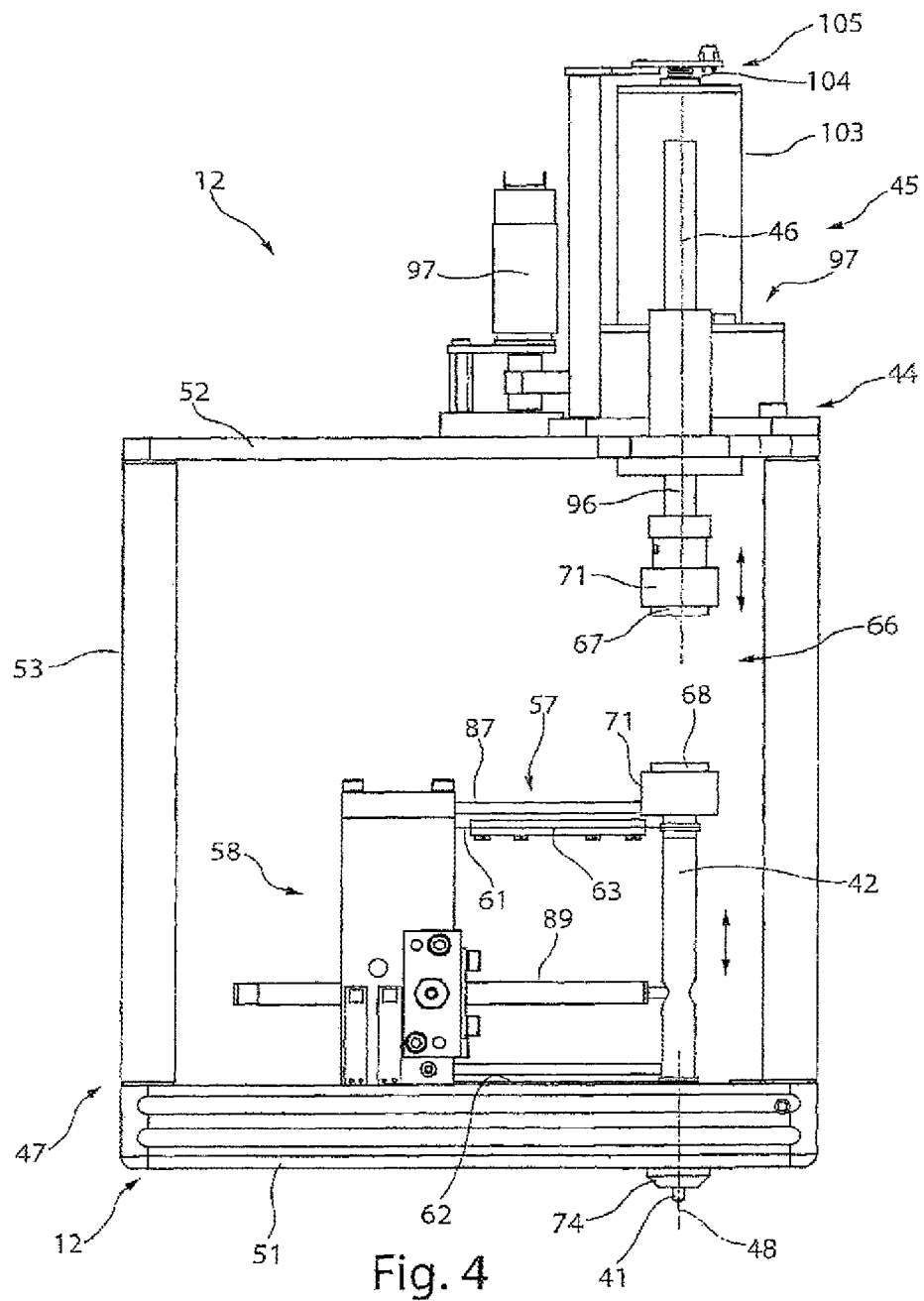

FIG. 2 illustrates a first perspective view of the measuring device 12 according to the invention. FIG. 3 illustrates another perspective view from below onto the measuring device 12 according to FIG. 2. FIG. 4 illustrates a schematic side view of the measuring device 12 according to FIG. 2, to which reference is likewise made in order to set out the structure of the measuring device 12.

The measuring device 12 includes a housing 47 with a base plate 51. Opposite said base plate, a cover element 52 is provided. Spacer elements 53 are provided between the base plate 51 and the cover element 52. The side walls between the base plate 51 and the cover element 52, which close the housing 47, are not illustrated for the purpose of clarity.

The base plate 51 comprises a recess 55, through which an indenter 41 extends and can exit downwards, as is illustrated in FIG. 3. The indenter 41 is received by a transmission element 42. Said element protrudes into an inner space of the housing 47. The transmission element 42 is preferably accommodated by a guide 57 within the housing 47. By means of said guide 57, the transmission element 43 can be moved up and down along a longitudinal axis 43 of the transmission element 42. The longitudinal axis 43 of the transmission element 42 corresponds to a longitudinal axis 48 of the indenter 41.

The guide 57, which accommodates the transmission element 42, is arranged on a holding device 58 fastened to the base plate 51. The guide 57 includes, for example, a first and second leaf spring elements 61, 62 oriented in perpendicular to the longitudinal axis 43 of the transmission element 42. The longitudinal axis 43 of the transmission element 42 is preferably situated in a travel axis 46 of a drive element 96 of the drive device 45 or is oriented in parallel thereto. The leaf-spring elements 61, 62 are preferably oriented in X-direction inside the housing, whereby the transmission element 42 is kept oriented in Z direction. Through these leaf-spring elements 61, 62, an up-and-down movement, or a travel movement along the Z axis of the housing 47 is allowed for. According to a first embodiment, it is provided that the leaf spring elements 61, 62 are formed from a thin, flat strip, in particular a spring steel. In order to reinforce the upper leaf spring element 61, for example, reinforcing elements 63 are fastened to an upper and lower side of the leaf spring element 61, 62. These reinforcing elements 63 can likewise be formed strip-shaped. Preferably, they are fixedly arranged on the leaf spring element 61 by means of a screw or a clipping connection. Alternatively, the upper leaf spring element 61 can also be configured thicker, that is more reinforced, so that the reinforcing elements are dispensable.

The measuring device 12 furthermore comprises a force generation means 44 which consists of a drive device 45 that is fastened to the cover element 52, for example.

Moreover, the force generation means 44 includes a magnetic transmission means 66, which comprises at least a first and a second magnetic pole 67, 68. A first magnetic pole 67 is assigned to the drive means 45. The at least one second magnetic pole 68 is arranged on an end of the transmission element 42 opposite the indenter 41. The first and the second magnetic pole 67, 68 are located in a common longitudinal axis, in particular in a travel axis 46 of the drive element 96, which element is preferably located in a Z axis of the housing. The first and the second magnetic pole 67, 68 are oriented to one another in such a manner that they are facing each other with a same pole. A repelling effect is thereby given between the magnetic poles 67, 68. The repelling effect or the magnetic force increases with a reducing distance of the two magnetic poles 67, 68 to one another. The magnetic poles 67, 68 are preferably configured as permanent magnets. The magnetic transmission means 66 allows for a contactless transmission of force from the drive element 96 of the drive device 45 onto the indenter 41. This magnetic transmission means 66 can also be referred to as a magnetic spring. Through the magnetic poles 67, 68 facing towards one another in opposite polarity a displacing movement is generated in a feed movement of the drive element 96 onto the transmission element 42. However, no rigid coupling is given, so that an excessive load in the components generating the displacing movement of the indenter 41 is prevented.

Figure 5:
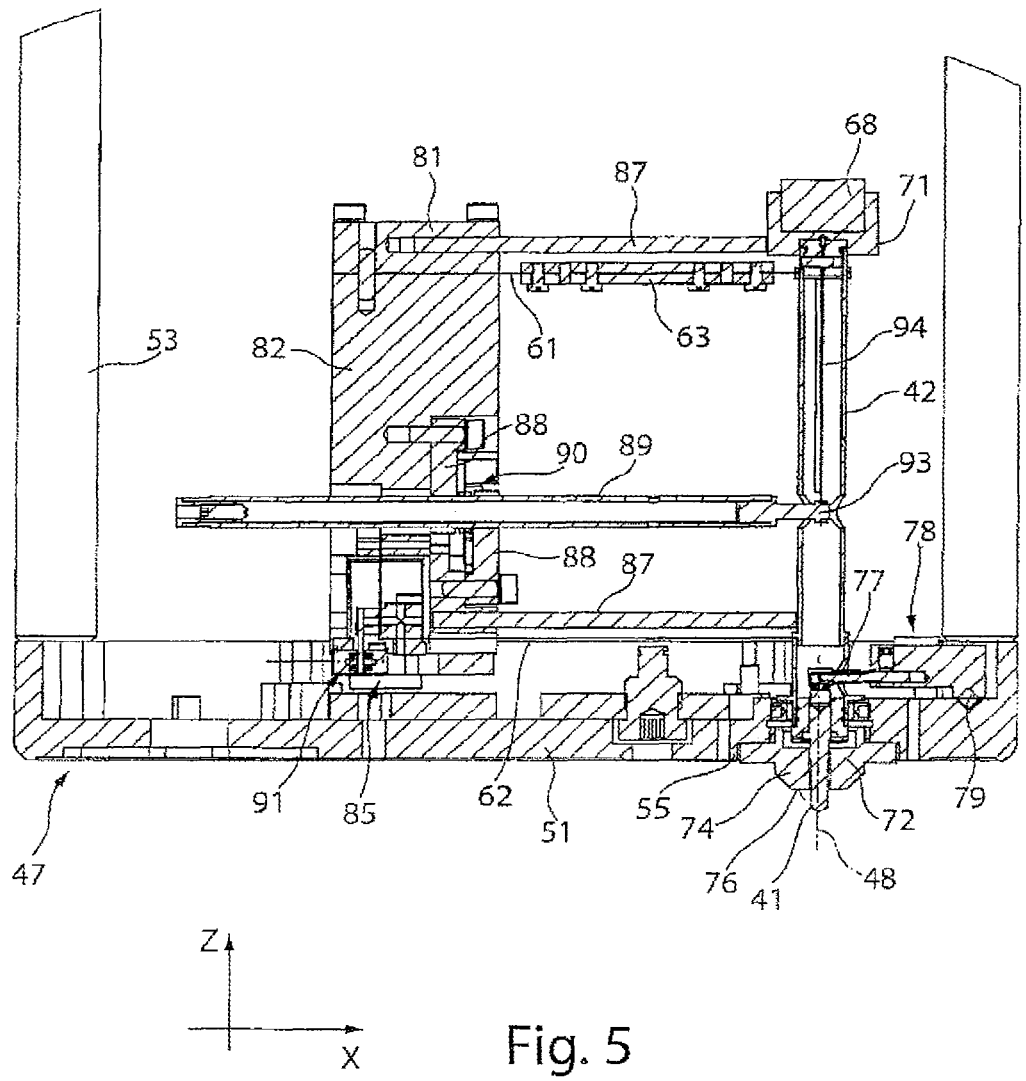

Reference is made to FIG. 5 for the purpose of further illustration of the transmission element 42 receiving the indenter 41, as well as the structure of the holding device 58 and the configuration of the guide 47.

The transmission element 42 is preferably formed as a tube. A receiving means 71 is provided on the upper end thereof, which receives the second magnetic pole 68. In this case, it can be a pot-shaped element, preferably from synthetic material. The magnetic pole 68 can, for example, be glued-in or pressed-in and is guided laterally in the receiving means 71. Preferably, the magnetic pole 68 is of cylindrical design. The longitudinal axis of the magnetic pole 68 is preferably oriented to the longitudinal axis 43 of the transmission element 42. Similar applies for the first magnetic pole 67. The indenter 41 is provided on the opposite end of the transmission element 42. Said indenter is accommodated in an exchangeable manner by a fastening means 72. In the configuration of the measuring device 12 as a hardness measuring device, the fastening means 72 can merely be provided by means of a latching or clipping connection, so that an axial securing of the indenter 41 in the fastening means 72 is provided. In the use of the measuring device 12 for determining the scratch resistance, the fastening means 72 also comprises a radial clamping in addition to the axial securing. Said securing can be provide by means of a threaded screw or the like. The fastening means 72 can in particular be configured as a collet chuck system.

The lower end of the transmission element 42 plunges into the recess 55 of the base plate 51, in a contact-free manner. An attachment ring 74 is positioned in this recess 55, through which ring the indenter 41 is guided through freely and without friction, such that the tip thereof can freely exit downwards. The tip of the indenter 41 is selected depending upon the measurement to be performed. Said tip can be in the shape of a pyramid or of a truncated cone. In the event of performing a scratch resistance measurement, the indenter 41 is oriented specifically within the fastening means 72.

A measuring probe 77 of a first measuring means 78 is provided at the inner end of the indenter 41. Said probe protrudes through an opening in the transmission element 42 and into the transmission element 42. This first measuring means 78 is preferably configured as a distance sensor and fastened to the base plate 51. The adjusting of a distance of the measuring probe 77 relative to the inner end of the indenter 51 is possible by means of an adjustment assembly 79. By means of this first measuring means 78, a distance of the indenter 41 to the measuring probe 47 is detected, beginning from an initial position to a penetration position and forwarded to the control 33.

Preferably the first measuring means 78 is a distance sensor, adjacent to the recess in the base plate of the housing, which device comprises a measuring probe or first sensor element 77 attached to an internal end of the indenter and a second sensor element included in the adjustment assembly 79. During a displacing movement or a penetrating movement of the indenter into the specimen, the actual displacing movement can thereby be detected by the distance between the first and second sensor elements. In one embodiment the first sensor element is a ferrite ring and the second sensor element comprises a coil and an eddy current is generated when the first sensor moves relative to the second sensor element. The eddy current is digitized and sent to the control device to determine the distance moved by the indenter. In another embodiment the first sensor element includes an optical encoded strip such as a grating or reticle and the second sensor element includes an optical sensor. The signal from the optical sensor is digitized and sent to the control device 33 to calculate the distance moved by the indenter. The first measuring means includes a first sensor that moves with the indenter and a second sensor fixed to the housing and the distance between the two sensor elements is determined either electronically or optically. The distance measurement data is sent to the control device.

By the guide 57 or the two leaf spring elements 61, 62 parallelly spaced from one another, a guided up-and-down movement of the transmission element 42 and thusly of the indenter 41 along the Z axis or the travel axis 46 can be achieved. The upper leaf-spring element 61 is held on the holding device 58 in a clamped manner. A fastening plate 81 is fastened to a mounting block 82 by a releasable connection, in particular screw connection, for example. A depression 83 can be provided for the defined alignment of the leaf spring element 61 in the mounting block 82, by means of which depression the leaf spring element 61 is aligned along an X axis of the housing 47.

The lower leaf-spring element 62 is mounted in the mounting block 82 by means of a clamping means 85. This clamping means 85 is subsequently described in greater detail in FIG. 8.

FIG. 5 furthermore shows a transport securing means 87 by means of two rods arranged on the holding device 58. The upper rod is arranged at a very small distance to the receiving means 71. The lower rod 87 terminates, with very minimal distance, in front of the transmission element 42. This way, already small deflections are blocked during transport.

Furthermore, two U-shaped plates 88 are provided in the mounting block 82 and oriented in opposite directions, which plates can secure a compensating element 89 in a somewhat horizontal orientation or orientation in X direction, during transport.

This compensating element 89 can be additionally provided. In the configuration of the measuring device 12 as a pure hardness measuring apparatus, this compensating element 89 is not required. a further stiffening can thereby be created for determining the scratch resistance, which counteracts a deflecting movement of the indenter 41. The compensating element 89 is rotatably-mounted in the mounting block 82. Preferably, a strap mounting is provided, which allows for a pivotable arrangement of the compensating element 89 about the Y axis in the housing 47. An end 93 directed towards the transmission element 42 preferably protrudes through an opening into the transmission element 42. Another leaf spring element 94 acts on this end 93, the opposite end of which element being fixed to the upper end of the transmission element 42. This leaf spring element 94 can, in turn, be of reinforced design. Preferably, the compensating element 89 is of tubular design.

Figure 6:
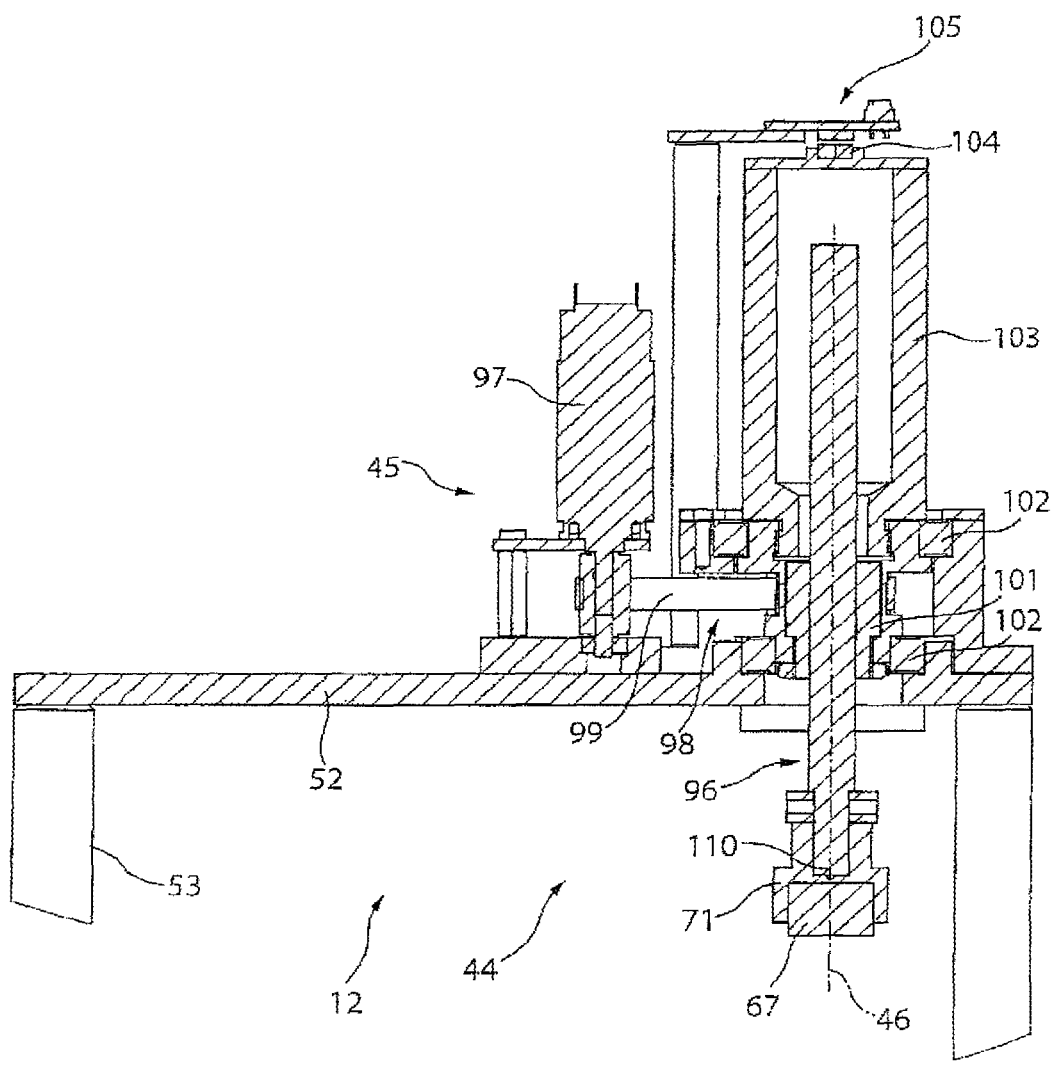
Figure 7:
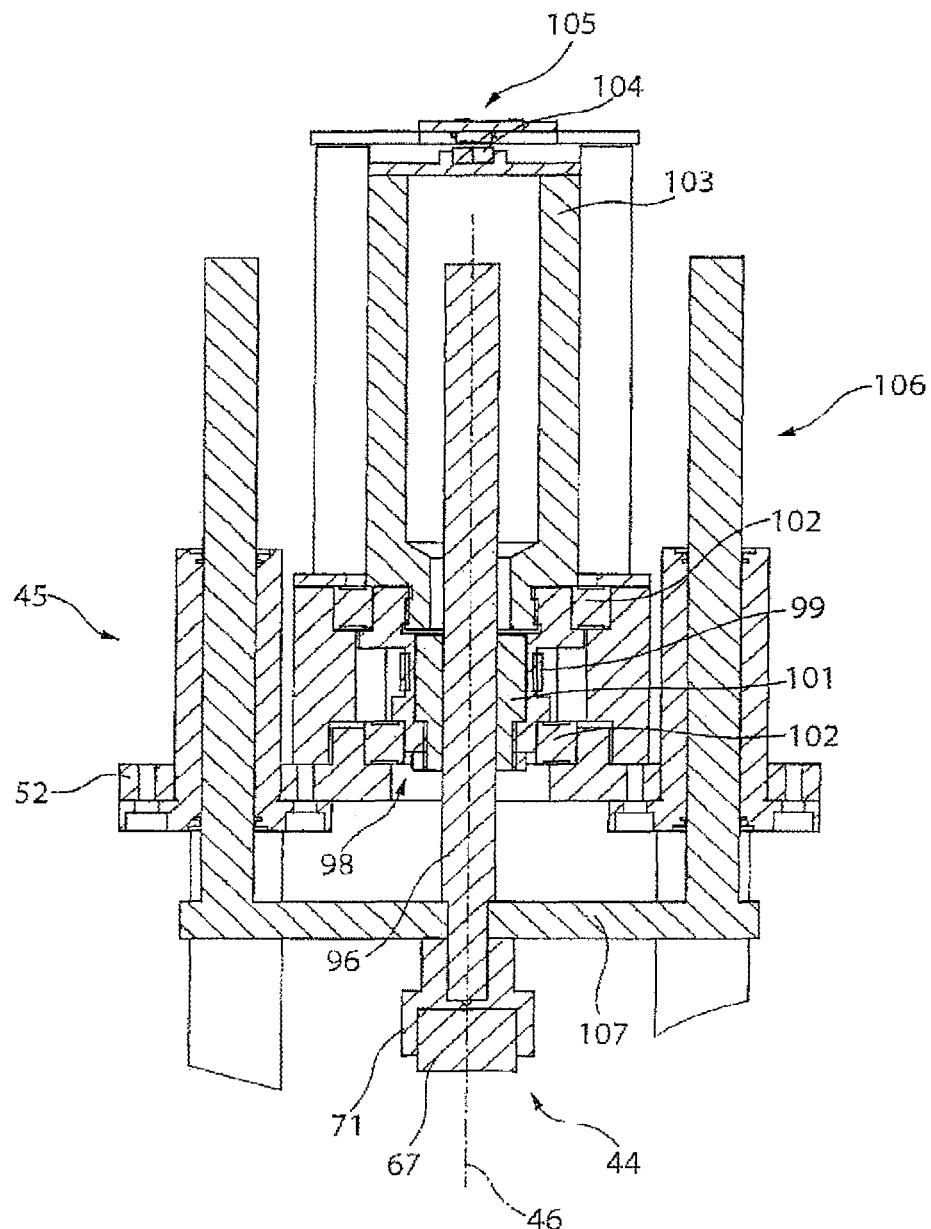

FIG. 6 illustrates the drive device 45 schematically and enlarged in a first side view, and FIG. 7 illustrates it in a second side view, rotated by 90° C. compared to the first side view in FIG. 7. The drive device 45 comprises a first drive element 96, in particular configured as a drive spindle. A receiving means 71 for receiving the first magnetic pole is provided at the lower free end of the drive element 95.

Preferably, the receiving means 71 for the first and second magnetic poles 67, 68 are identical. The arrangements of the first and the second magnetic poles 67, 68 can also be inverted.

In each case one magnetic pole 67, 68 can be provided in the receiving means 71, which is, one the one hand, provided on the transmission element 42 and, on the other hand, on the drive element 96. In addition, the receiving means 71 can be configured such that multiple, individual magnetic poles can be arranged therein. Just as well, the magnetic poles can, instead of an adhesive connection, be held by means of a latching or clipping connection, e.g. by an additional locking element, that engages on the receiving means 71.

The magnetic poles 67, 68 are advantageously of cylindrical design. Other geometries are also possible. Moreover, the magnetic poles 67, 68 can also be configured as rings with an internal through bore.

A drive motor 97 is provided for driving a displacing movement of the drive element 96 along the travel axis or the Z axis of the housing 47. An electric motor, in particular a servomotor, is advantageously provided. This drive motor 97 powers a rotary drive 98, which connects the drive motor 97 with the drive element 96. The rotary drive 98 e.g. includes a toothed belt 99 that drives a pinion on a drive shaft of the drive motor 97 and opposite on a rotatably-mounted spindle nut 101. The spindle nut 101 is rotatably accommodated by means of a bearing 102. The spindle nut 101 has a sleeve 103 provided thereon in a rotationally-secured manner, which sleeve accommodates a component 104 of a third measuring means 105 at an upper end. The third measuring means 105 is connected to the housing 47 in a stationary manner. The third measuring means 105 is preferably configured as a rotary encoder or incremental encoder, through which the rotation performed of the spindle nut 101 is determined.

A column guide 106 is provided for the rotationally-secured up-and-down-movement of the drive element 96. This column guide is fastened on the cover element 52 and includes a U-shaped guide column 107.

Preferably, a fourth measuring means 110 is provided between the magnetic pole 67 and the receiving device 71, or between the receiving device 72 and the drive element 96, which means is preferably configured as a force sensor. This fourth measuring means 110 detects the force acting between the two magnetic poles 67, 68. This allows the provision of another measuring parameter to be monitored, in order to establish measuring results. In particular, a monitoring and, as the case may be, a correction of the penetration force can be determined. The force transmitted on to the indenter 41 can be calculated by a feed movement of the drive element 96, the travel path of which is detected by the third measuring means 105, due to the know magnetic force of the two magnetic poles 67, 68. A comparison of the actually acting force is possible by means of the fourth measuring means 110.

Figure 8:
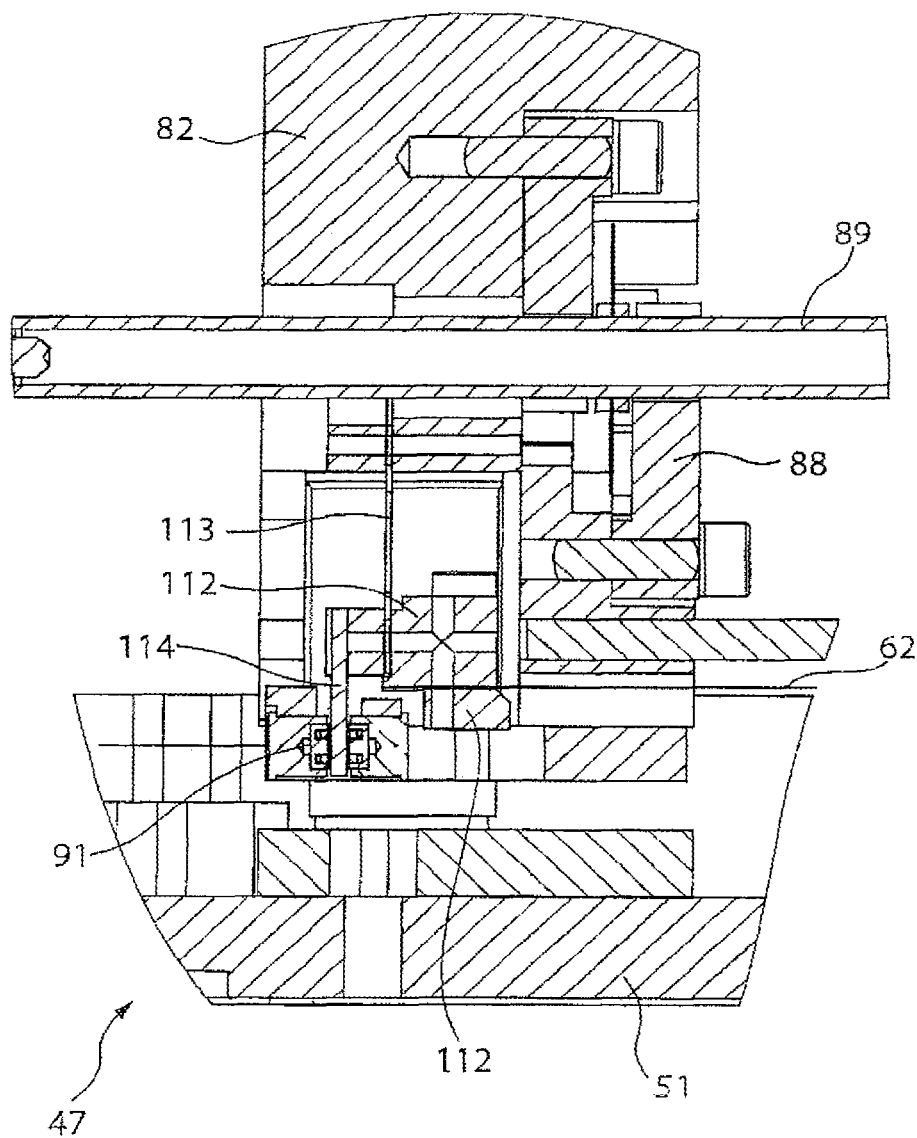

FIG. 8 illustrates the clamping means 85 in schematically enlarged illustration. The lower leaf spring element 62 is held on the end opposite the transmission element 42, in a clamped manner, by means of two clamping elements 112. These two clamping elements 112, in turn, are held on the mounting block 82 by means of another leaf spring element 113, with the leaf spring element 113 being oriented in the Z direction. This allows for a deflection movement of the lower leaf spring element 62 in and opposite the X direction. Furthermore, the clamping element 112 has a measuring vane 114, which plunges into a second measuring device 91. This measuring device 91, in turn, is configured as a distance sensor. A force or a displacing movement acting on the leaf spring element 62 can be measured by the second measuring device 91, by means of the shifting of the vane 114. This force or travel movement is transmitted to the leaf-spring element 62 via the indenter 41 and the transmission element 42. In particular when measuring the scratch resistance, this second measuring means 91 can detect another parameter regarding the deflection of the indenter 41.

The second measuring device operates on the same principles as the first measuring device already described. In one embodiment a ferrite ring is attached to the vane 114 and the second sensor element includes a coil such that the second measuring device is an eddy current detector. In another embodiment the vane 114 includes an optically encoded strip and the second sensor element includes an optical detector. The second measuring means includes a first sensor that moves with deflection of the indenter and a second sensor fixed to the housing and the distance between the two sensor elements is determined either electronically or optically. The distance measurement data is sent to the control device.

Figure 9:
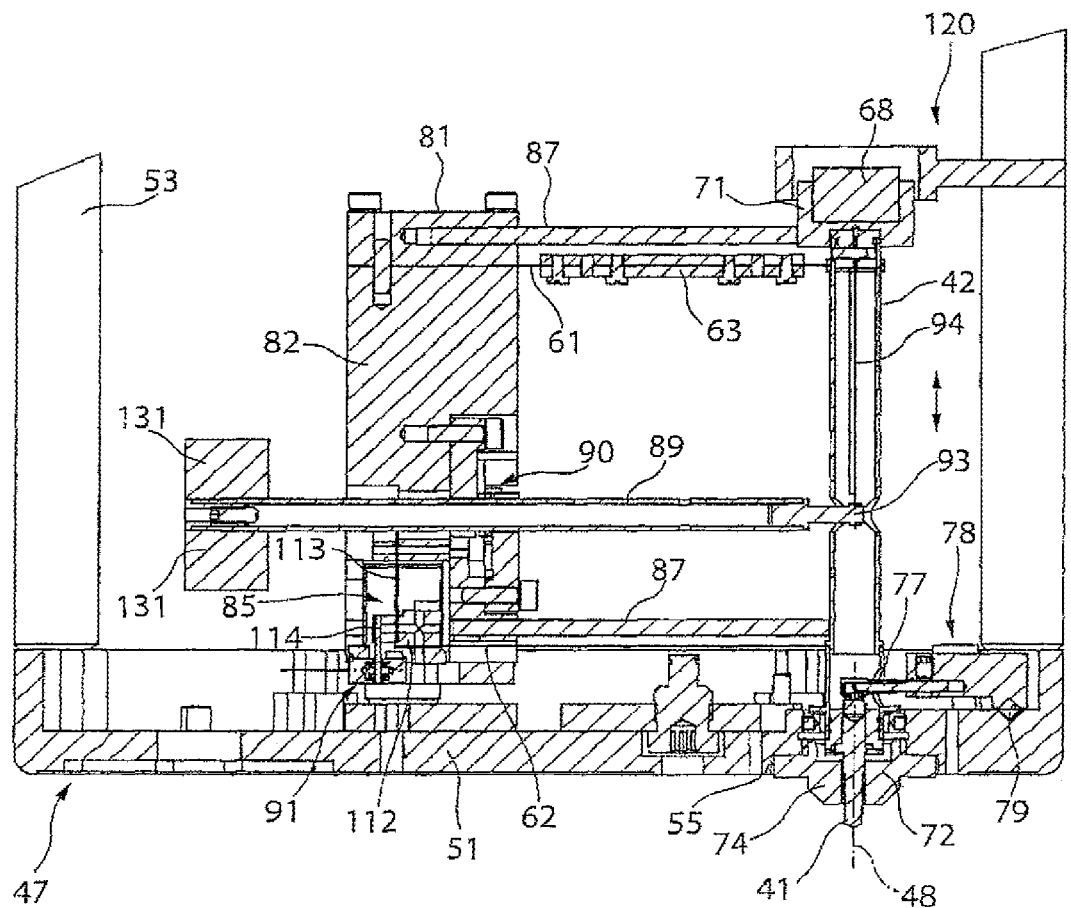

FIG. 9 is a schematic section of a lower part of the measuring device 12 according to an embodiment alternative to FIG. 5. This embodiment according to FIG. 9 mainly differs from the embodiment of FIG. 5 in that a vibration damping means 120 is assigned to the second magnetic pole 68, for example. Instead of this vibration damping means 120 assigned to the magnetic pole 68, a vibration damping means 130 also can be provided at an end of the compensating element 89 opposite the transmission element 42. A combination of the two is also possible. The vibration damping means 120, 130 fulfil the task of counteracting one or multiple lift-off movements of the indenter 41 directly after the indenter being placed on to a surface of the specimen 14. Preferably, so-called eddy current breaks are used.

The vibration damping means 120 is configured as an encasing 121, for example, which is preferably formed as a tube portion. This encasing encloses the magnetic pole 68. The magnetic pole 68 is preferably at least partially positioned inside the encasing 121, in an initial position. Once a lift-off movement takes place in the direction of the Z axis or the longitudinal axis 43, the magnetic pole 68 plunges into the encasing 121, whereby a counteracting magnetic force is increased. The encasing 121 is preferably formed of a ferromagnetic material, in particular copper. Preferably, the encasing 121 is adjustable in height relative to the magnetic pole 68. The encasing 121 can preferably be displaced in height along the spacer element 53.

The vibration damping means 130 is only illustrated in part. The compensating element 89 has a vane 131 provided thereon, formed of a ferromagnetic material. This vane is positioned between two mutually spaced permanent magnets, in order to act as a magnetic eddy current brake then.

Figure 10:
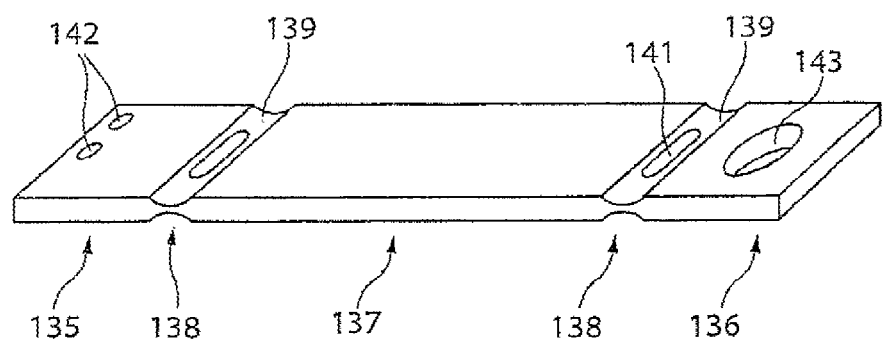

FIG. 10 is an enlarged schematic illustration of an alternative embodiment of a leaf-spring element 61, 62. Said leaf-spring element 61, 62 does not require a reinforcing element 63. Rather, the constructive design is selected such, that such an element can be dispensed with. The leaf-spring element 61 comprises a clamping region 135 and a connecting region 136, and a spacer portion 137 located therebetween. A flexure bearing 138 is formed between the clamping region 135 and the spacer region 137 as well as between the spacer region 137 and the connecting region 136. Said flexure bearing 138 is reduced in thickness with respect to the clamping region 135, connecting region 136 and spacer region 137. A hinge is formed thereby. Adjusting of the rigidity of the flexure bearing is on the one hand achieved with the reduce in thickness, as well as the design of the radiuses 139. In addition, one or multiple slot recesses 141 can be provided, in order to form softer flexure bearings 138. Instead of a planar design, the spacer portion 137 can also be configured as a frame or a supporting structure. Holes 142 are provided for aligning the leaf spring element 61 on the holding device, in order to secure-by-pin the clamping region 135 with the mounting block 82. Opposite and on the connecting region 136 is provided a receiving hole 143, in which the transmission element 42 can be positioned. The connecting region 136 and the transmission element 42 are preferably connected to one another by an adhesive connection.

Figure 11:
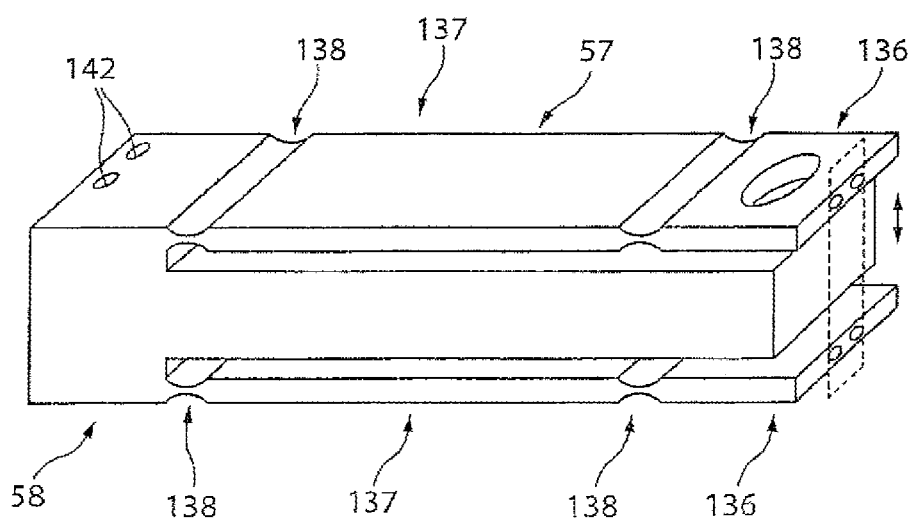

FIG. 11 illustrates an alternative embodiment of the guide 57 and the holding device 58. It is provided in this embodiment that the guide 57 and the holding device 58 are in one piece. Through a machining of the guide 57 out of one workpiece body, e.g. through eroding or ultrafine processing, it is made possible for the clamping region 135 to be integrally connected with the holding device 58, in particular the mounting block 82, and nonetheless for the leaf spring elements 61, 62 to be configured with the flexure bearings 138, the spacer portion 137 and the connecting region 136. A supporting body 146 extends between the leaf spring elements 61, 62. Said body restricts a deflecting movement of the transmission element 42 along the longitudinal axis 43, 48 or in Z-direction. The other two, face-side ends of the connecting regions 136 are fixedly connected with the transmission element 43, so that both an upward and downward movement—i.e. in and against the Z direction—is restricted.

To summarize the embodiment, a measuring device (11) for detecting measuring signals during a movement of an indenter (41) on a surface of a specimen (14), the measuring signals used to determine: a surface profile, a hardness, and, a scratch resistance of the specimen, is described, the measuring device (11) comprising:
   a) a housing, and,
   b) a control device (33) including a computer processor, computer memory, a user interface, and, input/output ports, and,
   c) a measuring table receptacle (26) that clamps the specimen (14) and whose position relative to the housing is controlled by the control device, and,
   d) a force-generation means (44) which is connected with an indenter (41) for generating a displacing movement of the indenter along a travel axis (48) of the indenter, the travel axis perpendicular to a surface of the specimen, and, the force-generation means is controlled by the control device and drives a penetrating movement of the indenter into the surface of the specimen, or, which positions the indenter on the surface of the specimen for scanning, and,
   e) the force generation means comprises a drive device (45) and a magnetic transmission device, and,
   f) the magnetic transmission device comprises a first magnetic pole (67) and a second magnetic pole (68), which are arranged at a distance to one another and which are oriented with the same poles to one other, and,
   g) the first magnetic pole is connected with the drive device that drives a displacing movement of the first magnetic pole along the travel axis or parallel thereto, or along an axis perpendicular to the travel, and,
   h) the second magnetic pole of the transmission device is connected to a first end of a transmission element, the second end of the transmission element, located opposite the first end, is connected to the indenter, and, wherein the transmission element is displaceably guided inside the housing along the travel axis, upon the displacing movement of the first magnetic pole by the drive device, and, i) thereby the movement of the drive device is transmitted on to the indenter by means of a magnetic force of the magnetic transmission device and the control device is programmed to determine a force of the indenter acting on the surface of the specimen, and, j) a first measuring means (78) for measuring a penetration depth of the indenter into the surface of the specimen or for measuring a displacing movement of the indenter along the travel axis during a scanning movement of the indenter across the surface of the specimen, the first measuring means comprising a first sensor element (77) attached to the indenter and a second sensor element included in an adjustment assembly (79), and, during a displacing movement of the indenter, the displacing movement is detected by the distance between the first and second sensor elements, and, k) wherein the first sensor element is a ferrite ring and the second sensor element comprises a coil, or, the first sensor element is an optical encoder and the second sensor element is an optical detector and an electrical signal from the second sensor element is sent to the control device which is programmed to determine the distance between the first and second sensor element based upon the electrical signal from the second sensor, and, l) wherein the transmission element is displaceably held in the housing by means of a guide connected to a holding device, and the guide comprises at least two leaf-spring elements (61, 62) spaced from one another, and, extending perpendicular from the transmission element to the holding device and which displaceably guides the transmission element along the travel axis, and, a second measuring means (91) comprising a second pair of sensor elements: a third sensor element (114) attached to an end of one of the at least two leaf-spring element connected to the holding device the indenter and a fourth sensor element fixed in the second measuring means (91), and, during a scanning movement of the indenter, a deflection movement of the indenter is detected by the distance between the third and fourth sensor elements, and, m) wherein the third sensor element is a ferrite ring and the fourth sensor element comprises a coil, or, the third sensor element is an optical encoder and the fourth sensor element is an optical detector and an electrical signal from the fourth sensor element is sent to the control device which determines the distance between the third and the fourth sensor element, and, n) a third measuring means (105) that measures a rotational movement of the drive device and thereby measures displacement of the first magnetic pole by the drive device, and, o) electrical signals from the first, second and third measuring means are received by the control device, and, the control device is further programmed to determine at least one of: a surface profile, a hardness, and, a scratch resistance of the specimen based upon the electrical signals.

Figure 12:
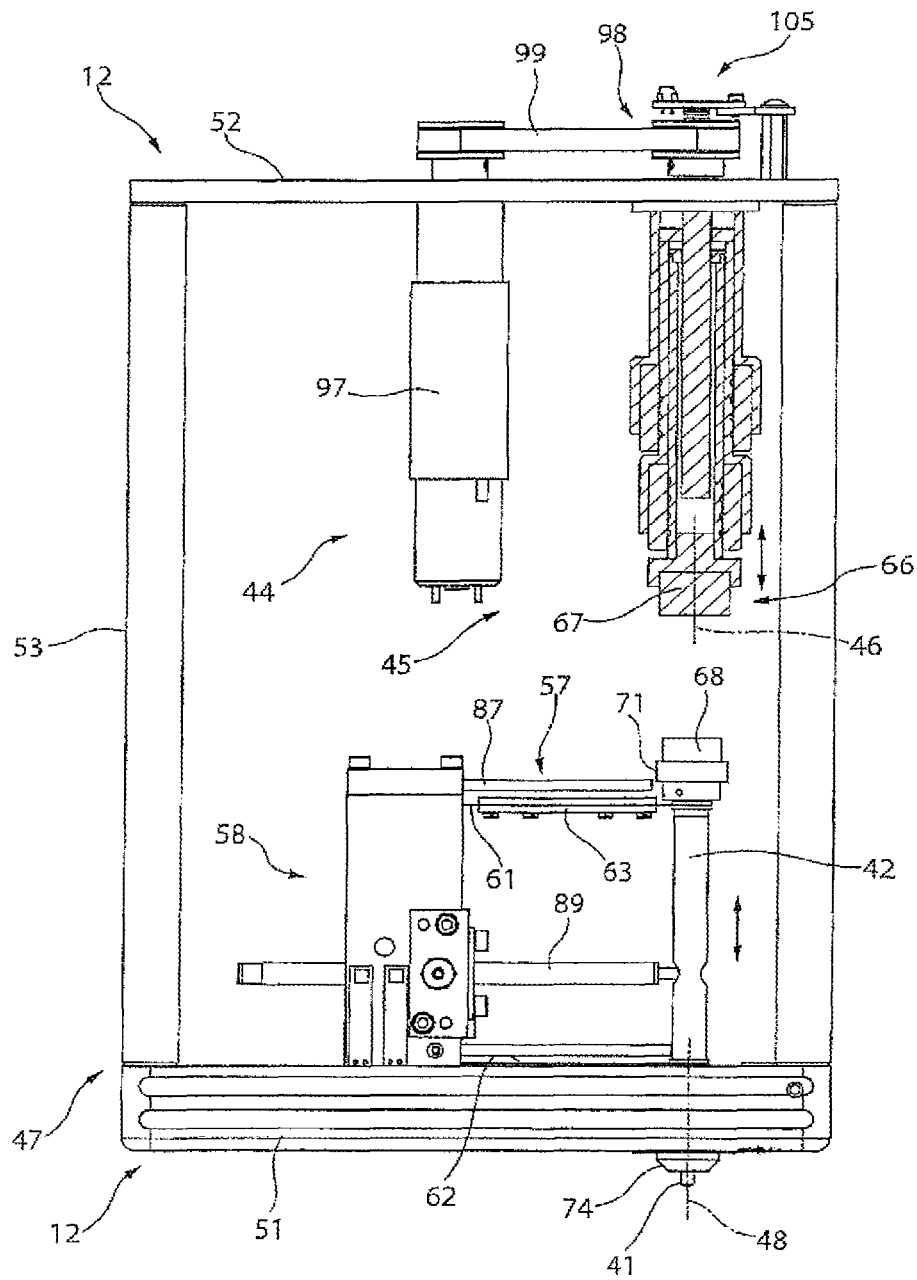

FIG. 12 illustrates a schematic side view of an embodiment of the measuring device 12 alternative to the above described measuring means. This measuring device 12 is configured differently in terms of the drive device 45 compared to the structure in particular described in FIGS. 6 and 7. The drive motor 97 of the drive device 45 is not provided outside, but inside a base body 16 of the measuring device 12. That is, the drive motor 97 is arranged internally, that is, on a lower side of the cover element 52. Also, the drive element 96 is fastened internally and on a lower side of the cover element 52. In this embodiment, the drive element 96 is configured as a so-called telescopic spindle. This telescopic spindle comprises a central drive spindle driven by means of the rotary drive 98 via a toothed belt 99 by the drive motor 97. This achieves a telescopic extension movement of the telescopic spindle, so that the receiving device 71 arranged at the lower, free end thereof with the first magnetic pole 67 is moved towards the opposite magnetic pole 68.

Figure 13:
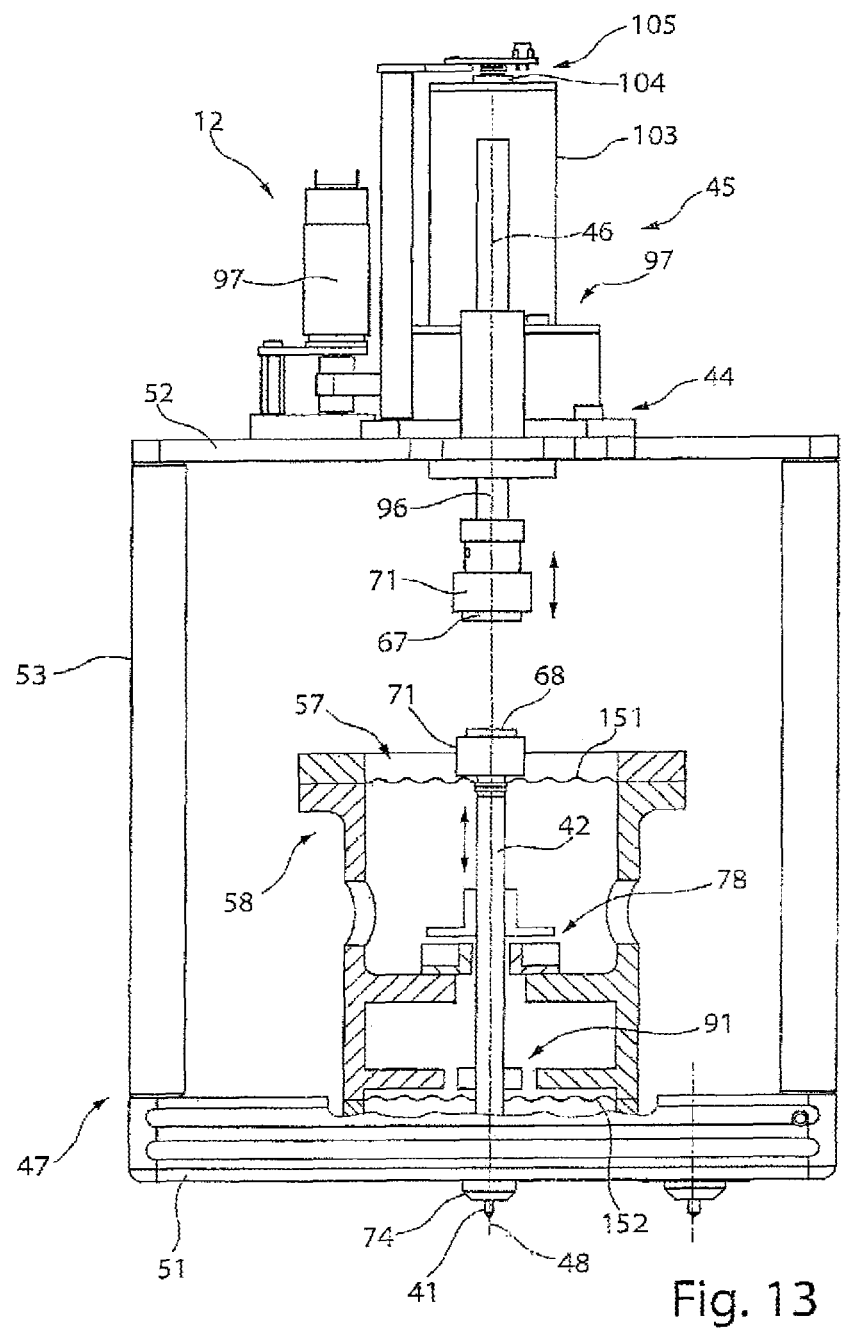

This embodiment of the measuring device 12 comes with the advantage of a lower construction height. The rotary drive 98 located outside the housing can be protected by means of a cover (not illustrated in greater detail here). FIG. 13 illustrates an embodiment alternative to FIG. 2 of the measuring device 12. This measuring device 12 comprises a guide 57 for the transmission element 42 that differs from the above-described exemplary embodiments. In this embodiment, the holding device 58 preferably is of cylindrical design and receives respectively one pressure diaphragm element 151, 152 on the upper and lower ends. Due to the parallelly-spaced arrangement of the pressure diaphragm elements 151, 152, a displacing movement along the travel axis 48 is effected under the impact of the magnetic force via the magnetic transmission device 66 or the second magnetic pole 67 on to the second magnetic pole 68 arranged on the transmission element 42 by means of the receiving device 71. The indenter 41 is moved coaxially relative to the attachment ring 74 downwards or outwards. A penetration movement of the indenter 41 in the measuring surface of the object to be measured. The pressure diaphragm element 151, 152 can be of wave-like design in a cross-section. When viewed in a top view, this means that concentric circles are provided. The degree of freedom of the deflection movement or the deflection force along the travel axis 48 can be defined by means of the number and the height of the waves. The pressure diaphragm elements 151, 152 are preferably made of a non-magnetic material. Said elements consist of a thin, disc-shaped, resilient material.

The first measuring means 78 is provided on the transmission means, with a sensor element of the measuring means 78 being fixedly arranged on the transmission element and the complementary sensor element of the measuring means 78 being fixedly arranged on the holding device 58. By a displacing movement along the travel axis 48, the distance between the two sensor elements is changed, thereby allowing a precise determination of the travel path. This first measuring means 78 operates similarly to the above described, first measuring device 78. The first measuring means using the capacitance between the two sensor elements to measure a distance as is well known in the art.

Preferably, a second measuring means 91 is arranged on the transmission element 42. The second measuring means 91 likewise comprises a sensor element directly on the transmission element 42 and, adjacent thereto, a second sensor element arranged on the holding device 58. A deviation in the deflection of the indenter 41 during a travel movement in the X direction or opposite the X direction can be detected by means of this second measuring means 91. The configuration of the second measuring means 91 corresponds to the measuring means 91 described in FIG. 9. The second measuring means using the capacitance between the two sensor elements to measure a distance as is well known in the art.

Figure 14:
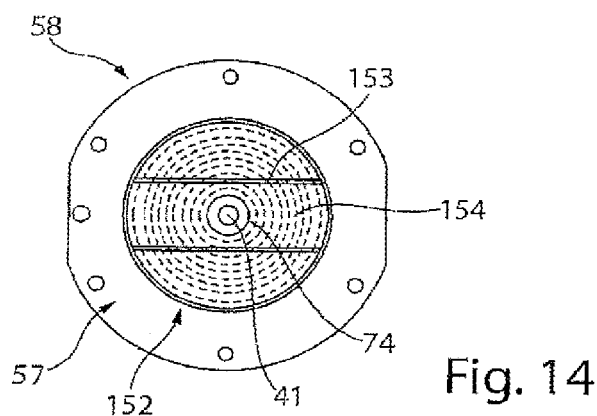

FIG. 14 is a schematic illustration from below on to the lower or the second pressure diaphragm element 152, which is oriented close to the indenter 41. The holding device 58 receives the pressure diaphragm element 152 preferably in a clamped manner. The concentric waves of the pressure diaphragm element 152, also provided in the pressure diaphragm element 151, are illustrated in a dashed manner. Furthermore, this lower pressure diaphragm element 152 comprises, in contrast to the upper pressure diaphragm element 151, two longitudinal slots 152 spaced parallel from one another. The longitudinal slots 152 are oriented in the X direction, or extend parallelly to the X axis, respectively. This is why the pressure diaphragm element 152 is configured to be soft or resilient along the Y axis, and rigid in the X axis. As a result, a deflection of the indenter 41 in the X direction can be detected during the measuring of the scratch resistance.

In the embodiment according to FIG. 13, similar to the second measuring means 91, another measuring means can be provided on the transmission pin 42, arranged offset by 90°. This way, a deflection movement of the indenter 41 can be detected in the Y-direction.

Reference is made in the following to the above-described embodiments and alternatives.

Figure 15:
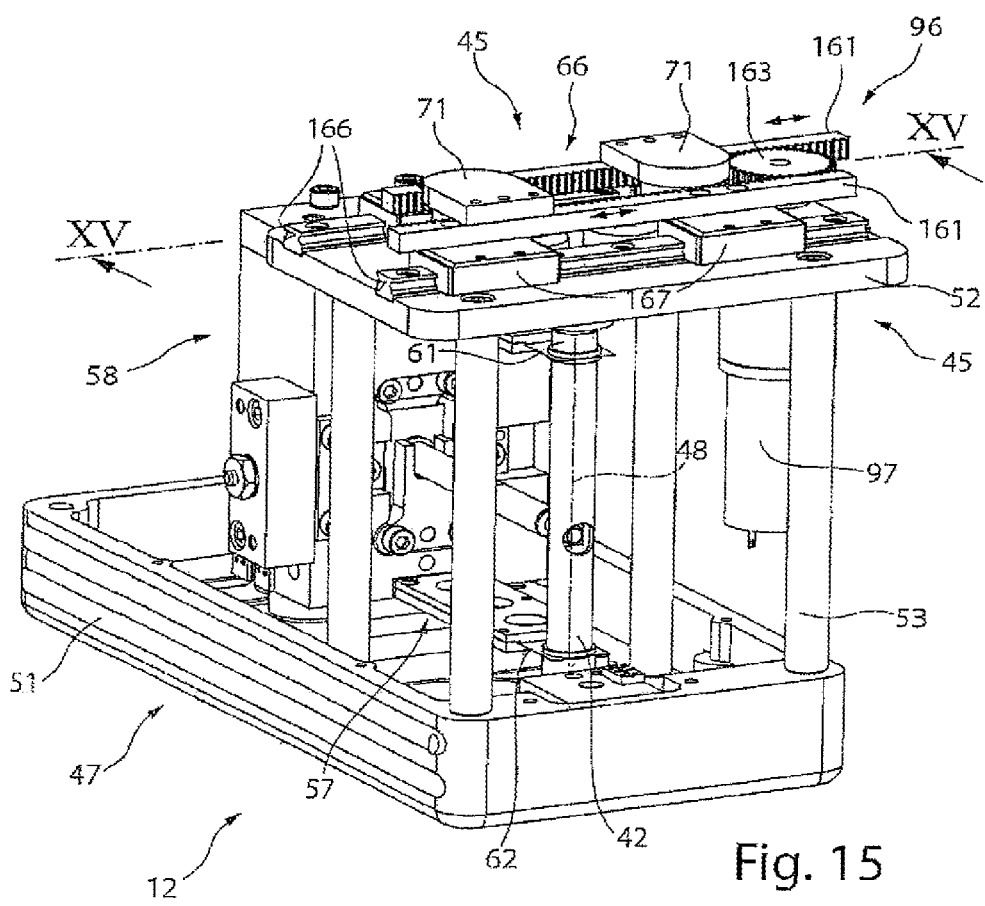
Figure 16:
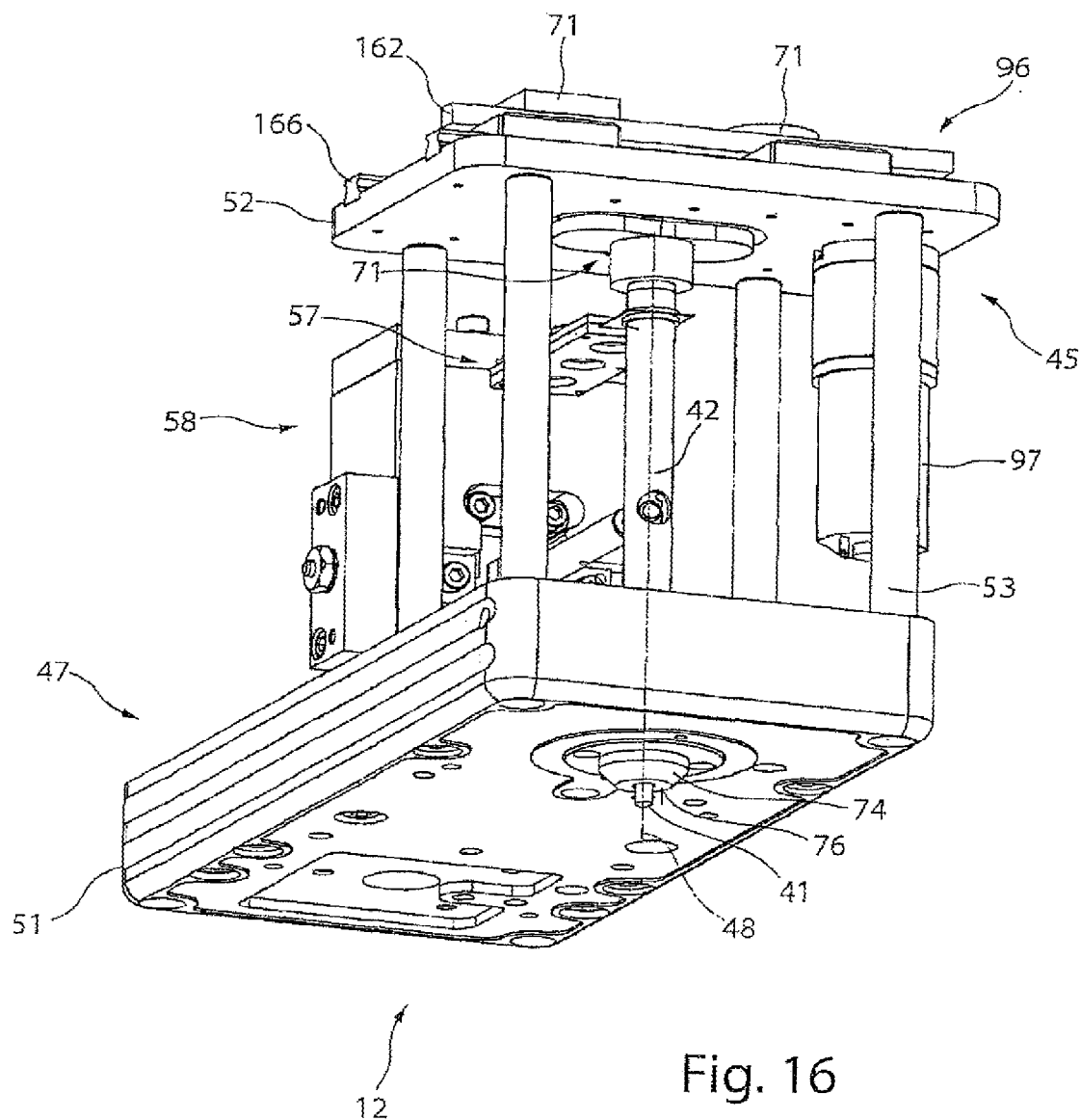

FIG. 15 illustrates a first perspective view of another embodiment alternative to the embodiment of FIG. 2 of the measuring device 12. FIG. 16 shows another perspective view of the alternative embodiment of the measuring device 12 according to FIG. 15.

Figure 17:
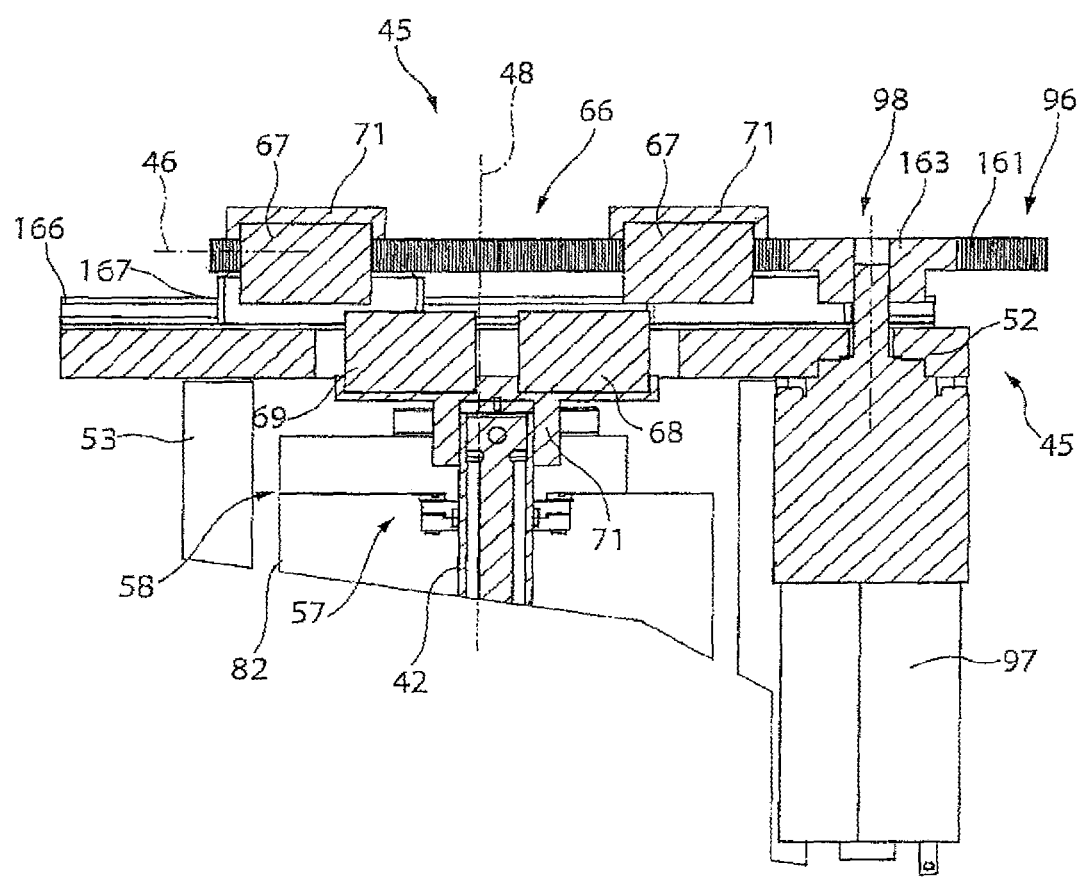

This measuring device 12 differs from the first embodiment according to FIG. 2 in that the drive device 45 of the force generation means 44 is configured differently. For the purpose of better illustration, FIG. 17 shows a schematic sectional view of this alternative embodiment of the drive device 45.

The drive device 45 of this alternative embodiment is arranged on the housing 47, in particular the cover element 52. The drive motor 97 powers a drive element 96 formed by two toothed racks 161, 162 oriented in parallel to one another. This pair of toothed racks 161, 162 is powered by a drive wheel 163, which wheel is, in turn, rotatively-connected with the drive motor 97. Said drive wheel 163 is preferably provided directly on the drive shaft of the drive motor 97. Alternatively, a gear mechanism for reduction or transmission can be provided therebetween. This drive wheel 163 at the same time powers both toothed racks 161, 162. This induces an opposite displacing movement of the toothed racks 161, 162.

The rotary movement of the drive shaft of the drive motor 97 or of the drive wheel 163 can be detected or decoded in a simple manner, so that thereupon, due to the fixed geometric relations of drive wheel 163 and toothed rack 161, 162, an exact detection and driving of the travel path of the permanent magnets of the first magnetic pole 67 is made possible.

The displacing movement of the toothed racks 161, 162 takes place along a travel axis 46, which axis is oriented perpendicularly to the travel axis 48 of the transmission element 42 or the indenter 41. In the exemplary embodiment, the travel axis 48 is thus oriented in Z direction—that is, in the vertical—and the travel axis 46 is oriented in the X/Y plane, respectively the horizontal.

The drive element 96 is displaceably accommodated by means of a guide 165. The guide 165 preferably consists of two guide rails 166 oriented in parallel to one another, guiding one or multiple displaceable carriages 167. In each case one toothed rack 161, 162 is arranged on the carriage(es) 167.

It provided in this alternative embodiment for the first magnetic pole 67 to be formed of two separate permanent magnets. Alternatively, also multiple, separate permanent magnets can be provided. The second magnetic pole 68 is adapted to the first permanent magnet 67 in terms of the number of the separate permanent magnets. The receiving means 71 on the transmission element 42 comprises two separate depressions, which, at a same distance to the travel axis 48, receive the permanent magnets for forming the second magnetic pole 68.

The receiving device 71 for receiving the first magnetic pole 67 is formed by two receiving elements 71 arranged separately to one another. Each receiving element 71 for the permanent magnet is arranged on a toothed rack 161, 162, wherein these are in each case oriented such, that the receiving means 71 is positioned between the two toothed racks 161, 162 extending in parallel.

In an initial position of the measuring device 12, the two permanent magnets of the first magnetic pole 67 are spaced from one another in such a way, that said magnets do not or almost not impart any magnetic force on to the oppositely arranged permanent magnets of the second magnetic pole 68. For driving the penetrating movement of the indenter 41, a rotary movement is induced into the drive wheel 73 by means of the drive motor 97, through which wheel the two toothed racks 161, 162 are driven synchronously and displaced oppositely to one another. The two permanent magnets of the first magnetic pole 67 are simultaneously moved towards one another. In a position of the permanent magnets of the first magnetic pole 67 relative to those of the second magnetic pole 68, as is illustrated in FIG. 17, only a small magnetic force is transmitted, because of the small degree of overlap. The maximum transmission of force exists if the permanent magnets of the first magnetic pole 67 are moved towards one another in such a way until they are positioned to be congruent with the permanent magnets of the second magnetic pole 68. The degree of overlap is driven by a control of the measuring device 12, in particular depending on a penetration movement or depending on the travel path of the indenter 41.

Alternatively to the above displacing movement of the permanent magnets of the first magnetic pole 67 for driving the penetration movement of the indenter 41, it can also be provided that the permanent magnets of the first magnetic pole 67 are located adjacently next one another in an initial position, and that the permanent magnets of the second magnetic pole 68, at a large distance, are located outside the two permanent magnets of the first magnetic pole 67, which are arranged so as to directly neighbor one another. In this case, a displacing movement of the permanent magnets of the first magnetic pole 67 is driven to lead them away from one another.

In the embodiments illustrated in FIGS. 15 to 17, the travel axis 46 is e.g. oriented according to the coordinate system illustrated in FIG. 2. Alternatively, this travel axis 46 can also be oriented in another direction within the XY plane, in particular in the X axis.

According to another embodiment (not shown in greater detail) of the measuring device 12 according to FIG. 15, it can also be provided, that the first and the second magnetic poles 67, 68 consist only of one permanent magnet. Therefore, driving of only one drive element having the first magnetic pole 67 fixed to it, is sufficient in order to displace said pole along the travel axis 46 perpendicular to the travel axis 48 of the transmission element.

Furthermore, it can alternatively be provided, that e.g. more than two permanent magnets are provided per magnetic pole 67, 68. Said magnets can then be arranged on a circumference of a circle. This way, multiple permanent magnets of the first magnetic pole 67 can be brought in partial or complete overlap with respect to the respective permanent magnets of the second magnetic pole 68, by means of a pivot movement.

Incidentally, the above-described embodiments and alternatives apply directly or analogously also for the above-described measuring device 12 according to FIGS. 15 to 17.

The above-described measuring devices 12 allow both for measurement in an upright position, as is illustrated in the Figures, as well as an overhead measuring.

Performing of the hardness measuring of a surface of the specimen 14 with a measuring device 12 in a measuring arrangement 11 is effected as follows: After having placed the specimen 14 on to the measuring table 26, the measuring device 12 is positioned above the specimen 14 by means of the stand 17. In this initial position of the measuring device 12, the indenter 41 is in an initial position, that is, the indenter 41 is set back relative to an underside of the base plate 51 of the housing or relative to a place-on surface 76 on the attachment ring 74 fixed to the housing 47. Subsequently, the measuring device 12 is moved towards the surface of the specimen 14 by means of the at least one motor 19 of the stand 17. When placing on a place-on surface 76 of the attachment ring 74 of the measuring device 12 on to the specimen 14, the feed movement is immobilized. Subsequently the force generation means 44 is activated. The drive means 45 actuates the drive element 96, so that the latter performs a displacing movement along the travel axis 46 in the direction towards the indenter 41. Due to the magnetic transmission device 66, the magnetic pole 67 is moved towards the magnetic pole 68. Due to the repelling magnetic force of the two magnetic poles 67, 68, the feed movement along the travel axis 46 is transmitted contactless from the magnetic pole 67 on to magnetic pole 68. By means of this guide 57, the indenter 41 is moved along the travel axis 46, which is preferably congruent with the longitudinal axis 43 of the transmission element 42 downwards and towards the surface of the specimen 14. Once the indenter 41 comes to rest on the surface of the specimen 14, the first measuring means 78 does not determine any change in distance, so that the feed movement of the drive means 45 is immobilized via the control 33. This initial position is forwarded to the control 33 as zero position. Subsequently, another feed movement of the drive element 96 is driven by means of the control 33, thereby driving a penetration movement of the indenter 41 into the specimen 14. The first measuring means 78 determines the penetration path. The test force can be determined from the feed movement of the drive element 96, which movement is detected by a third measuring means 105. Alternatively and/or for comparison, the testing force acting on the indenter 41 can also be determined by means of the fourth measuring means 110. From these measured values and the geometry of the indenter 41, the hardness of the surface of specimen 14 can be determined. The indenter 41 can be in the form of a sphere or a pyramid. This indenter preferably consists of diamond, topaz, corundum or quartz.

Subsequently, the measuring device 12 is lifted-off the specimen 14 and/or the drive element 96 is driven to perform a displacing movement oppositely to the indenter 41. This can be effected simultaneously, or one after the other. The measuring device 12 is returned to an initial position. Using the guide 47, the indenter 41 is likewise set back into an initial position with the transmission pin 42.

Subsequently, after having introduced a penetration location into the specimen 14, a mapping of the penetration location can be established by means of the optical detection device, and an optical assessment can be performed as well.

For determining the scratch resistance of a surface of a specimen 14, the specimen 14 is positioned on the measuring table 25 or on a measuring table receptable 26 of the measuring table 15. Above the specimen 14 the measuring device 12 is positioned, so that an indenter, by means of a feed movement perpendicular to the surface of the specimen 14, can be moved towards said specimen. The drive device 45 is actuated, so that the drive element 96 performs a feed movement along the travel axis 46 in the direction towards the indenter 41. This feed movement is transformed into a displacing movement of the indenter 41 by means of the magnetic transmission device 66, so that the indenter is transferred from an initial position into an operating position. In this operating position, the indenter 41 protrudes with respect to a lower side of the base plate 51 of the housing 47 or of an attachment ring 47 arranged in the recess 55 of the baseplate 51 of the housing 47.

Thereafter, the measuring device 12 is moved towards the specimen 14. This is e.g. effected by means of the motor 19. Once the indenter 41 is placed on the surface of the specimen 14, the feed movement is immobilized. This contact is detected by the first measuring means 78. The measuring device 12 is arranged in a starting position to the specimen 14. This starting position is stored in the control 33 as the zero position. This starting position can be intended for a so-called pre-scan to determine the scratch resistance. Said starting position can also be intended for a measuring of the surface roughness of the specimen.

Based on this starting position, first a pre-scan can be performed, i.e. the surface of the specimen 14 is scanned along a predetermined displacement path of the surface of the specimen 14. The displacement path is oriented tangentially or rectangularly to the specimen 14, for example along the X axis. Preferably, the measuring device 12 is immobile and the measuring table 25 is displaced by means of a motor 28 in the direction of arrow 27 according to FIG. 1, thereby scanning the position of the surface and the contour of the surface and storing the measuring signals as pre-scratch profile data, also referred to as pre-scan. Thereafter, the measuring device 12 is lifted-off the specimen 14. The measuring device 12 and the measuring table 25 are positioned back into the starting position. Thereupon, again by means of the control 33, the same displacing movement as with the pre-scan according to arrow 27 is driven using the motor 28. Simultaneously with this displacing movement, drive means 45 is driven, so that the indenter is applied with a testing force, whereby the indenter 41 increasingly penetrates into the surface of the specimen 41 during the displacing movement of the measuring table 25. This penetration movement is detected by the first measuring device 48. At the same time, the applied testing force is calculated using the third measuring device 105. In addition, the actually applied testing force can be detected by means of the fourth measuring means 110. In addition thereto, a deflection of the indenter 41 in the travel direction according to arrow 27 is detected by means of the second measuring means 91. At the end of the predefined displacing movement after the application of the predefined testing force, the measuring device is, in turn, lifted-off the specimen 14. The measuring signals detected during the introducing of a scratch are stored by the control 33 and assessed in order to determine the scratch resistance.

The measuring device 12 and the measuring table 25 can again be returned into the starting position. Thereafter, a so-called post-scan can take place. The indenter 41 is positioned in the scratch. Again, a displacing movement of the measuring table 25 is effected according to arrow 27, whereby the indenter 41 is guided along the scratch and into the scratch. Again, a travel movement of the measuring table 25 according to arrow 27 takes place, thereby guiding the indenter 41 along the scratch and in the scratch. During the displacing movement of the indenter 41 in the scratch, the measuring signals are again detected by the first measuring means 78 and at least the second measuring means 91. In addition thereto, a deflection of the indenter in Y-direction, i.e. in a direction perpendicular to the X-direction in the plane of the surface of the specimen 14, can be detected during the pre-scan, the introduction of the scratch and/or the post-scan by means of another sensor of another measuring means. After the introduction of the scratch and/or after the post scan, the optical detection means 29 can detect the scratch and additionally allow for an optical evaluation.

In order to measure the surface roughness of the specimen 14 the starting position is taken again, just as with measuring the scratch resistance. Starting from this starting position, the indenter 41 is moved along a predetermined displacement path on the surface of the specimen 14. The displacement path is oriented tangentially or rectangularly to the specimen 14 and along the X axis. In this case, the measuring device 12 can be immobilized and the measuring table is displaced in the direction of arrow 27 by means of a motor 28. Alternatively, the measuring table can be immobile and the measuring device 12 is displaced. Just as well, a relative movement can be effected between these two. The displacement movement of the indenter 41 along the longitudinal axis 48 caused by the surface roughness of the specimen 14 is detected by the first measuring means 78 and assessed by the control 33. After the scan of a predetermined displacement path along the surface of the specimen 14, the measuring device 12, in turn, is lifted-off the specimen 14.

I claim:

1. A measuring device for detecting measuring signals during a movement of an indenter on a surface of a specimen, the measuring signals used to determine: a surface profile, a hardness, and, a scratch resistance of the specimen, the measuring device comprising:
    a) a housing, and,
    b) a control device including a computer processor, computer memory, a user interface, and, input/output ports, and,
    c) a measuring table receptacle that clamps the specimen and whose position relative to the housing is controlled by the control device, and,
    d) a force-generation means which is connected with an indenter for generating a displacing movement of the indenter along a travel axis of the indenter, the travel axis perpendicular to a surface of the specimen, and, the force-generation means is controlled by the control device and drives a penetrating movement of the indenter into the surface of the specimen, or, which positions the indenter on the surface of the specimen for scanning, and,
    e) the force generation means comprises a drive device and a magnetic transmission device, and,
    f) the magnetic transmission device comprises a first magnetic pole and a second magnetic pole, which are arranged at a distance to one another and which are oriented with the same poles to one other, and,
    g) the first magnetic pole is connected with the drive device that drives a displacing movement of the first magnetic pole along the travel axis or parallel thereto, or along an axis perpendicular to the travel, and,
    h) the second magnetic pole of the transmission device is connected to a first end of a transmission element, the second end of the transmission element, located opposite the first end, is connected to the indenter, and, wherein the transmission element is displaceably guided inside the housing along the travel axis, upon the displacing movement of the first magnetic pole by the drive device, and,
    i) thereby the movement of the drive device is transmitted on to the indenter by means of a magnetic force of the magnetic transmission device and the control device is programmed to determine a force of the indenter acting on the surface of the specimen, and,
    j) a first measuring means, configured as a distance sensor, for measuring a penetration depth of the indenter into the surface of the specimen or for measuring a displacing movement of the indenter along the travel axis during a scanning movement of the indenter across the surface of the specimen,
    k) a second measuring means is configured as a distance sensor and, during a scanning movement of the indenter, a deflection movement of the indenter perpendicular to the displacement movement of the indenter is detected by the distance sensor, and,
    l) a third measuring means that measures a rotational movement of the drive device and thereby measures displacement of the first magnetic pole by the drive device, and,
    m) electrical signals from the first, second and third measuring means are received by the control device, and, the control device is further programmed to determine at least one of: a surface profile, a hardness, and, a scratch resistance of the specimen based upon the electrical signals.

2. The measuring device according to claim 1, by the displacing movement of the first magnetic pole in the direction towards the second magnetic pole, the displacing movement of the indenter, a penetration force into the specimen, and, a contact force on the specimen for scanning the surface of the specimen are adjusted by the control device.

3. The measuring device according to claim 1, wherein the housing comprises a base plate with a recess, and the travel axis is aligned with the recess, and the indenter, is positioned, from an initial position inside the recess or inside an attachment ring arranged in the recess, to a second position with the indenter protruding to an outer side of the base plate and wherein a guide holds the transmission element with the indenter arranged thereon in the initial position.

4. The measuring device according to claim 1, wherein the first measuring means is provided on the baseplate of the housing adjacent to the indenter.

5. The measuring device according to claim 1, wherein the drive device is provided on a cover element of the housing, which comprises at least one drive element displaceable along the travel axis, or parallel to the travel axis, and the drive element receives the first magnetic pole at an end directed towards the transmission element.

6. The measuring device according to claim 5, wherein the drive element is guided, as a drive spindle with a guide provided on the housing, in a manner secured against rotation, or that the drive element is configured as a telescopic spindle and that the drive element is connected with a rotary drive driven by a drive motor.

7. The measuring device according to claim 1, wherein the drive element is oriented perpendicular to the travel axis, and the drive element drives a simultaneous displacing movement of two or more permanent magnets forming the first magnetic pole to an overlapping position with respect to a corresponding number of permanent magnets forming the second magnetic pole.

8. The measuring device according to claim 7, wherein the drive element is formed by a pair of toothed racks, which are actuatable with a rotary drive, the toothed racks oriented perpendicular to the travel axis and displaceable along guide rails thereby providing the displacing movement of the two or more permanent magnets forming the first magnetic pole.

9. The measuring device according to claim 1, further comprising a vibration damping device, wherein the vibration damping device is formed as an enclosure made of a ferromagnetic material, which surrounds the second magnetic pole, and, the second magnetic pole is at least partially contained in the enclosure.

10. The measuring device according to claim 1, further comprising a compensating element having an elongated shape with a first end and a second end and located between and parallel to the at least two leaf spring elements, and, the first end of the compensating element is pivotably mounted on a holding device and the second end of the compensating element protrudes into the transmission element and is connected through use of a leaf-spring-connector to the first end of the transmission element.

11. The measuring device according to claim 10, further comprising two U-shaped clamps, within the holding device that, when actuated, clamp the compensating element in position for transport.

12. The measuring device according to claim 1, further including an optical detection means arranged on the housing, wherein the measuring table receptacle is displaced between the measuring device and the optical detection means, driven by the control device.

13. The measuring device according to claim 1, wherein the first measuring means comprises a first sensor element attached to the indenter and a second sensor element included in an adjustment assembly, and, during a displacing movement of the indenter, the displacing movement is detected by the distance between the first and second sensor elements, and, wherein the first sensor element is a ferrite ring and the second sensor element comprises a coil, or, the first sensor element is an optical encoder and the second sensor element is an optical detector and an electrical signal from the second sensor element is sent to the control device which is programmed to determine the distance between the first and second sensor elements based upon the electrical signal from the second sensor.

14. The measuring device of claim 1, wherein the transmission element is displaceably held in the housing by means of a guide connected to a holding device, and the guide comprises at least two leaf-spring elements spaced from one another or two spaced-apart pressure membrane elements, and, extending perpendicular from the transmission element to the holding device and which displaceably guides the transmission element along the travel axis.

15. A measuring device (11) for detecting measuring signals during a movement of an indenter (41) on a surface of a specimen (14), the measuring signals used to determine: a surface profile, a hardness, and, a scratch resistance of the specimen, the measuring device (11) comprising:

a) a housing, and, b) a control device (33) including a computer processor, computer memory, a user interface, and, input/output ports, and, c) a measuring table receptacle (26) that clamps the specimen (14) and whose position relative to the housing is controlled by the control device, and, d) a force-generation means (44) which is connected with an indenter (41) for generating a displacing movement of the indenter along a travel axis (48) of the indenter, the travel axis perpendicular to a surface of the specimen, and, the force-generation means is controlled by the control device and drives a penetrating movement of the indenter into the surface of the specimen, or, which positions the indenter on the surface of the specimen for scanning, and, e) the force generation means comprises a drive device (45) and a magnetic transmission device, and, f) the magnetic transmission device comprises a first magnetic pole (67) and a second magnetic pole (68), which are arranged at a distance to one another and which are oriented with the same poles to one other, and, g) the first magnetic pole is connected with the drive device that drives a displacing movement of the first magnetic pole along the travel axis or parallel thereto, or along an axis perpendicular to the travel, and, h) the second magnetic pole of the transmission device is connected to a first end of a transmission element, the second end of the transmission element, located opposite the first end, is connected to the indenter, and, wherein the transmission element is displaceably guided inside the housing along the travel axis, upon the displacing movement of the first magnetic pole by the drive device, and, i) thereby the movement of the drive device is transmitted on to the indenter by means of a magnetic force of the magnetic transmission device and the control device is programmed to determine a force of the indenter acting on the surface of the specimen, and, j) a first measuring means (78) for measuring a penetration depth of the indenter into the surface of the specimen or for measuring a displacing movement of the indenter along the travel axis during a scanning movement of the indenter across the surface of the specimen, the first measuring means comprising a first sensor element (77) attached to the indenter and a second sensor element included in an adjustment assembly (79), and, during a displacing movement of the indenter, the displacing movement is detected by the distance between the first and second sensor elements, and, k) wherein the first sensor element is a ferrite ring and the second sensor element comprises a coil, or, the first sensor element is an optical encoder and the second sensor element is an optical detector and an electrical signal from the second sensor element is sent to the control device which is programmed to determine the distance between the first and second sensor element based upon the electrical signal from the second sensor, and, l) wherein the transmission element is displaceably held in the housing by means of a guide connected to a holding device, and the guide comprises at least two leaf-spring elements (61, 62) spaced from one another, and, extending perpendicular from the transmission element to the holding device and which displaceably guides the transmission element along the travel axis, and, a second measuring means (91) comprising a second pair of sensor elements: a third sensor element (114) attached to an end of one of the at least two leaf-spring element connected to the holding device the indenter and a fourth sensor element fixed in the second measuring means (91), and, during a scanning movement of the indenter, a deflection movement of the indenter is detected by the distance between the third and fourth sensor elements, and, m) wherein the third sensor element is a ferrite ring and the fourth sensor element comprises a coil, or, the third sensor element is an optical encoder and the fourth sensor element is an optical detector and an electrical signal from the fourth sensor element is sent to the control device which determines the distance between the third and the fourth sensor element, and, n) a third measuring means (105) that measures a rotational movement of the drive device and thereby measures displacement of the first magnetic pole by the drive device, and, o) electrical signals from the first, second and third measuring means are received by the control device, and, the control device is further programmed to determine at least one of: a surface profile, a hardness, and, a scratch resistance of the specimen based upon the electrical signals.

16. The measuring device according to claim 15, by the displacing movement of the first magnetic pole in the direction towards the second magnetic pole, the displacing movement of the indenter, a penetration force into the specimen, and, a contact force on the specimen for scanning the surface of the specimen are adjusted by the control device.

17. The measuring device according to claim 15, wherein the drive device is provided on a cover element of the housing, which comprises at least one drive element displaceable along the travel axis, or parallel to the travel axis, and the drive element receives the first magnetic pole at an end directed towards the transmission element.

18. The measuring device according to claim 17, wherein the drive element is guided, as a drive spindle with a guide provided on the housing, in a manner secured against rotation, or that the drive element is configured as a telescopic spindle and that the drive element is connected with a rotary drive driven by a drive motor.

19. The measuring device according to claim 17, wherein the drive element is oriented perpendicular to the travel axis, and the drive element drives a simultaneous displacing movement of two or more permanent magnets forming the first magnetic pole to an overlapping position with respect to a corresponding number of permanent magnets forming the second magnetic pole.

20. The measuring device according to claim 19, wherein the drive element is formed by a pair of toothed racks, which are actuatable with a rotary drive, the toothed racks oriented perpendicular to the travel axis and displaceable along guide rails thereby providing the displacing movement of the two or more permanent magnets forming the first magnetic pole.

* * * * *